(12) United States Patent  
Baker et al.

(10) Patent No.: US 10,179,896 B2  
(45) Date of Patent: Jan. 15, 2019

(54) METHOD AND SYSTEM FOR A BIOARTIFICIAL ORGAN

(71) Applicant: Baker Group, LLP, Portland, OR (US)

(72) Inventors: Michael John Baker, Portland, OR (US); Shelby K. Suckow, Portland, OR (US)

(73) Assignee: Baker Group, LLP, Portland, OR (US)

( * ) Notice: Subject to any disclaimer, the term of this patent is extended or adjusted under 35 U.S.C. 154(b) by 0 days.

(21) Appl. No.: 15/152,385

(22) Filed: May 11, 2016

(65) Prior Publication Data

US 2016/0333295 A1    Nov. 17, 2016

Related U.S. Application Data

(60) Provisional application No. 62/160,440, filed on May 12, 2015.

(51) Int. Cl.

| | |
|---|---|
| C12M 3/06 | (2006.01) |
| C12M 3/00 | (2006.01) |
| C12N 5/071 | (2010.01) |
| C12M 1/12 | (2006.01) |
| C12M 1/00 | (2006.01) |
| C12M 1/26 | (2006.01) |
| C12M 1/34 | (2006.01) |
| C12M 1/36 | (2006.01) |
| B01D 63/08 | (2006.01) |

(52) U.S. Cl.
CPC ............ *C12M 21/08* (2013.01); *C12M 23/16* (2013.01); *C12M 25/02* (2013.01); *C12M 29/00* (2013.01); *C12M 29/04* (2013.01); *C12M 33/04* (2013.01); *C12M 41/40* (2013.01); *C12M 41/48* (2013.01); *C12N 5/0697* (2013.01); *B01D 63/088* (2013.01)

(58) Field of Classification Search
CPC ...... C12M 21/08; C12M 23/16; C12M 23/40; C12M 23/58; C12M 25/02; C12M 29/04; B01D 63/08; B01D 63/082; B01D 63/088
See application file for complete search history.

(56) References Cited

U.S. PATENT DOCUMENTS

| | | |
|---|---|---|
| 5,270,192 A | 12/1993 | Li et al. |
| 5,955,353 A | 9/1999 | Amiot |
| 6,008,047 A | 12/1999 | Curcio et al. |

(Continued)

FOREIGN PATENT DOCUMENTS

| | | |
|---|---|---|
| CN | 1321175 C | 6/2007 |
| CN | 201793567 U | 4/2011 |

(Continued)

OTHER PUBLICATIONS

Tuhy et al. "Urea separation in flat-plate microchannel hemodialyzer; experiment and modeling." Biomed Microdevices, vol. 14 ( 2012), pp. 595-602. (Year: 2012).*

(Continued)

*Primary Examiner* — William H. Beisner  
(74) *Attorney, Agent, or Firm* — McCoy Russell LLP

(57) ABSTRACT

Methods and systems are provided for a stem cell organ device including an array of alternating stem cell channels and fluid channels. In one example, a method may include loading a stem cell channel with stem cells and flowing blood through a fluid channel in order to allow an exchange of molecules between the stem cells and the blood.

19 Claims, 20 Drawing Sheets

(56) References Cited

U.S. PATENT DOCUMENTS

| | | | |
|---|---|---|---|
| 6,069,005 | A | 5/2000 | Reid et al. |
| 6,146,889 | A | 11/2000 | Reid et al. |
| 6,372,495 | B1 | 4/2002 | Flendrig |
| 6,506,574 | B1 | 1/2003 | Rambhatla et al. |
| 6,858,146 | B1 | 2/2005 | Myers et al. |
| 6,946,293 | B1 | 9/2005 | Lu et al. |
| 6,979,308 | B1 | 12/2005 | MacDonald et al. |
| 7,048,856 | B2 | 5/2006 | Fissell, IV et al. |
| 7,150,990 | B2 | 12/2006 | Nakauchi et al. |
| 7,256,042 | B2 | 8/2007 | Rambhatla et al. |
| 7,282,366 | B2 | 10/2007 | Rambhatla et al. |
| 7,390,651 | B2 | 6/2008 | Triglia et al. |
| 7,534,601 | B2 | 5/2009 | Wikswo et al. |
| 7,655,070 | B1 | 2/2010 | Dallas et al. |
| 7,824,912 | B2 | 11/2010 | Sherley et al. |
| 8,062,632 | B2 | 11/2011 | Lee et al. |
| 8,105,491 | B2 | 1/2012 | Brotherton et al. |
| 8,119,774 | B2 | 2/2012 | Pera et al. |
| 8,143,009 | B2 | 3/2012 | Snodgrass |
| 8,163,536 | B2 | 4/2012 | Abuljadayel |
| 8,216,839 | B2 | 7/2012 | Lee et al. |
| 8,318,479 | B2 | 11/2012 | Domansky et al. |
| 8,329,457 | B2 | 12/2012 | Park et al. |
| 8,357,528 | B2 | 1/2013 | Vacanti et al. |
| 8,445,280 | B2 | 5/2013 | Neumann et al. |
| 8,460,546 | B2 | 6/2013 | Weinberg et al. |
| 8,535,923 | B2 | 9/2013 | Aleksandrova et al. |
| 8,557,571 | B2 | 10/2013 | Kugelmann et al. |
| 8,608,953 | B2 | 12/2013 | Brotherton et al. |
| 8,632,489 | B1 | 1/2014 | Ahmed |
| 8,647,861 | B2 | 2/2014 | Ingber et al. |
| 8,673,635 | B2 | 3/2014 | Sokal et al. |
| 8,691,523 | B2 | 4/2014 | Reid et al. |
| 8,715,954 | B2 | 5/2014 | Triglia et al. |
| 8,748,180 | B2 | 6/2014 | Shuler et al. |
| 8,785,117 | B2 | 7/2014 | Nyberg |
| 8,802,432 | B2 | 8/2014 | Zaret et al. |
| 8,981,046 | B2 | 3/2015 | Schaffer et al. |
| 2005/0158845 | A1 | 7/2005 | Wikswo et al. |
| 2007/0093562 | A1 | 4/2007 | Groth et al. |
| 2008/0220523 | A1 | 9/2008 | Antwiler |
| 2009/0124963 | A1* | 5/2009 | Hogard .................. A61M 1/16 604/30 |
| 2009/0131858 | A1 | 5/2009 | Fissell et al. |
| 2010/0326914 | A1 | 12/2010 | Drost et al. |
| 2011/0250585 | A1 | 10/2011 | Ingber et al. |
| 2012/0190113 | A1 | 7/2012 | Gao et al. |
| 2012/0196345 | A1 | 8/2012 | Zink et al. |
| 2013/0004386 | A1 | 1/2013 | Borenstein et al. |
| 2014/0051163 | A1 | 2/2014 | Healy et al. |
| 2014/0069861 | A1 | 3/2014 | Browning et al. |
| 2014/0076066 | A1 | 3/2014 | Harrington et al. |
| 2014/0093905 | A1 | 4/2014 | Ingber et al. |
| 2014/0093906 | A1 | 4/2014 | Ingber et al. |
| 2014/0120066 | A1 | 5/2014 | Yeghiazarians et al. |
| 2014/0147880 | A1 | 5/2014 | Ingber et al. |
| 2014/0209540 | A1 | 7/2014 | Smejtek et al. |
| 2014/0291243 | A1 | 10/2014 | Curtis et al. |
| 2014/0295548 | A1 | 10/2014 | Nyberg |
| 2014/0299545 | A1 | 10/2014 | Wrazel et al. |
| 2015/0004077 | A1 | 1/2015 | Wikswo et al. |
| 2015/0209783 | A1 | 7/2015 | Ingber et al. |
| 2015/0298123 | A1 | 10/2015 | Block, III et al. |
| 2015/0328386 | A1 | 11/2015 | Peterson et al. |
| 2016/0046896 | A1 | 2/2016 | Ingber et al. |

FOREIGN PATENT DOCUMENTS

| | | |
|---|---|---|
| CN | 101732771 B | 8/2011 |
| CN | 101624473 B | 10/2012 |
| CN | 103348001 A | 10/2013 |
| CN | 103952370 A | 7/2014 |
| CN | 204072913 U | 1/2015 |
| EP | 1783489 A1 | 5/2007 |
| EP | 1177829 B1 | 10/2007 |
| EP | 1824965 B1 | 10/2011 |
| JP | 2006217977 A | 8/2006 |
| JP | 4534046 B2 | 9/2010 |
| RU | 2513593 C2 | 4/2014 |
| TW | I427146 B | 2/2014 |
| WO | 3207615 A1 | 5/1992 |
| WO | 2004020341 A2 | 3/2004 |
| WO | 2005000376 A2 | 1/2005 |
| WO | 2006042079 A1 | 4/2006 |
| WO | 2010009307 A2 | 1/2010 |
| WO | 2010105204 A2 | 9/2010 |
| WO | 2010123357 A1 | 10/2010 |
| WO | 2010149597 A2 | 12/2010 |
| WO | 2010151419 A1 | 12/2010 |
| WO | 2011014674 A2 | 2/2011 |
| WO | 2011069110 A1 | 6/2011 |
| WO | 2011158125 A2 | 12/2011 |
| WO | 2012017337 A1 | 2/2012 |
| WO | 2012106459 A1 | 8/2012 |
| WO | 2012167051 A2 | 12/2012 |
| WO | 2012174460 A1 | 12/2012 |
| WO | 2013052680 A2 | 4/2013 |
| WO | 2013086486 A1 | 6/2013 |
| WO | 2013086505 A1 | 6/2013 |
| WO | 2014031532 A1 | 2/2014 |
| WO | 2014039514 A2 | 3/2014 |
| WO | 2014123600 A2 | 8/2014 |
| WO | 2014124527 A1 | 8/2014 |
| WO | 2014210364 A2 | 12/2014 |
| WO | 2015006751 A1 | 1/2015 |
| WO | 2015013210 A1 | 1/2015 |
| WO | 2015013332 A1 | 1/2015 |
| WO | 2015028577 A1 | 3/2015 |
| WO | 2015053834 A2 | 4/2015 |
| WO | 2015102726 A2 | 7/2015 |
| WO | 2015138032 A2 | 9/2015 |
| WO | 2015138034 A2 | 9/2015 |
| WO | 2016010861 A1 | 1/2016 |
| WO | 2016049363 A1 | 3/2016 |
| WO | 2016049365 A1 | 3/2016 |
| WO | 2016049367 A1 | 3/2016 |
| WO | 2016086040 A1 | 6/2016 |

OTHER PUBLICATIONS

Ding, Y. et al., "The development of a new bioartificial liver and its application in 12 acute liver failure patients," World Journal of Gastroenterology, vol. 9, No. 4, Apr. 2003, 4 pages.

Van De Kerkhove, M. et al., "Clinical Application of Bioartificial Liver Support Systems," Annals of Surgery, vol. 240, No. 2, Aug. 2004, 15 pages.

Mills, J. et al., "Technology Insight: liver support systems," Nature Clinical Practice: Gastroenterology & Hepatology, vol. 2, No. 9, Sep. 2005, 8 pages.

Chamuleau, R., "Future of bioartificial liver support," World Journal of Gastrointestinal Surgery, vol. 1, No. 1, Nov. 30, 2009, 5 pages.

Stange, J. et al., "Extracorporeal liver support," Organogenesis, vol. 7, No. 1, Jan. 2011, 10 pages.

Czysk, K. et al., "DMSO Efficiently Down Regulates Pluripotency Genes in Human Embryonic Stem Cells during Definitive Endoderm Derivation and Increases the Proficiency of Hepatic Differentiation," PLoS ONE, vol. 10, No. 2, Feb. 6, 2015, 16 pages.

Abaci, H. et al., "Pumpless microfluidic platform for drug testing on human skin equivalents," Lab on a Chip, vol. 15, No. 3, Feb. 7, 2015, 13 pages.

Glorioso, J. et al., "Pivotal preclinical trial of the spheroid reservoir bioartificial liver," Journal of Hepatology, vol. 63, No. 2, Aug. 2015, Published Online Mar. 25, 2015, 11 pages.

Abaci, H. et al., "Human-on-a-chip design strategies and principles for physiologically based pharmacokinetics/ pharmacodynamics modeling," Integrative Biology: Quantitative Biosciences from Nano to Macro, vol. 7, No. 4, Apr. 7, 2015, 16 pages.

Kamiya, A. et al., "Human pluripotent stem cell-derived cholangiocytes: current status and future applications," Current Opinion in Gastroenterology, vol. 31, No. 3, May 2015, 6 pages.

(56) References Cited

OTHER PUBLICATIONS

Esch, M. et al., "Multi-Cellular 3D Human Primary Liver Cell Cultures Elevate Metabolic Activity Under Fluidic Flow," Lab on a Chip, vol. 15, No. 10, May 21, 2015, 18 pages.
Oleaga, C. et al., "Multi-Organ toxicity demonstration in a functional human in vitro system composed of four organs," Natures: Scientific Reports, vol. 6, Feb. 3, 2016, 17 pages.
Intrator, M., "Request for Information from entities interested in commercializing Laboratory-developed advanced in vitro assessment technology," Los Alamos National Laboratory, Publication No. LA-UR-16-20441, Available Online at http://permalink.lanl.gov/object/tr?what=info:lanl-repo/lareport/LA-UR-16-20441, Mar. 30, 2016, 6 pages.
Nobourg, G. et al., "Liver Progenitor Cell Line HepaRG Differentiated in a Bioartificial Liver Effectively Supplies Liver Support to Rats with Acute Liver Failure," PLoS ONE, vol. 7, No. 6, Jun. 18, 2012, 8 pages.
Zhou L, et al., "Key challenges to the development of extracorporeal bioartificial liver support systems," Hepatobiliary & Pancreatic Diseases International, vol. 11, No. 3, Jun. 15, 2012, 7 pages.
Shi, X. et al., "Evaluation of a novel hybrid bioartificial liver based on a multi-layer flat-plate bioreactor," World Journal of Gastroenterology, vol. 18, No. 28, Jul. 28, 2012, 9 pages.
Xia, L. et al., "Hepatocyte function within a stacked double sandwich culture plate cylindrical bioreactor for bioartificial liver system," Biomaterials, vol. 33, No. 32, Nov. 2012, Published Online Aug. 11, 2012, 8 pages.
Pan, X. et al., "Establishment and characterization of immortalized human hepatocyte cell line for applications in bioartificial livers," Biotechnology Letters, vol. 34, No. 12, Dec. 2012, Published Online Aug. 29, 2012, 8 pages.
Kasuya, J. et al., "Microporous membrane-based liver tissue engineering for the reconstruction of three-dimensional functional liver tissues in vitro," Biomatter, vol. 2, No. 4, Oct. 2012, 6 pages.
Yang, Y. et al., "Co-Culture With Mesenchymal Stem Cells Enhances Metabolic Functions of Liver Cells in Bioartificial Liver System," Biotechnology and Bioengineering, vol. 110, No. 3, Mar. 2013, Published Online Nov. 1, 2012, 11 pages.
Iwamuro, M. et al., "A preliminary study for constructing a bioartificial liver device with induced pluripotent stem cell-derived hepatocytes," BioMedical Engineering OnLine, vol. 11, No. 93, Dec. 7, 2012, 12 pages.
Pan, X. et al., "Advances in cell sources of hepatocytes for bioartificial liver," Hepatobiliary & Pancreatic Diseases International, vol. 11, No. 6, Dec. 15, 2012, 12 pages.
Nibourg, G. et al., "Effect of acute-liver-failure-plasma exposure on hepatic functionality of HepaRG-AMC-Bioartificial Liver," Liver International, vol. 33, No. 4, Apr. 2013, Published Online Feb. 7, 2013, 10 pages.
Banares, R. et al., "Liver Support Systems: Will They Ever Reach Prime Time?," Current Gastroenterology Reports, vol. 15, No. 3, Mar. 2013, Published Online Feb. 8, 2013, 7 pages.
Palakkan, A. et al., "Evaluation of Polypropylene Hollow-Fiber Prototype Bioreactor for Bioartificial Liver," Tissue Engineering: Part A, vol. 19, No. 9-10, May 2013, Published Online Feb. 21, 2013, 11 pages.
Giri, S. et al., "Nanostructured self-assembling peptides as a defined extracellular matrix for long-term functional maintenance of primary hepatocytes in a bioartificial liver modular device," International Journal of Nanomedicine, vol. 3, Published Online Apr. 18, 2013, 15 pages.
Shi, G. et al., "Use of Perfluorocarbons to Enhance the Performance of Perfused Three-Dimensional Hepatic Cultures," Biotechnology Progress, vol. 29, No. 3, May 2013, Published Online Apr. 18, 2013, 9 pages.
Hilal-Alnaqbi, A. et al., "Experimental evaluation and theoretical modeling of oxygen transfer rate for the newly developed hollow fiber bioreactor with three compartments," Bio-Medical Materials and Engineering, vol. 23, No. 5, Available as Early as May 14, 2013, 18 pages.
Stevens, K. et al., "InVERT molding for scalable control of tissue microarchitecture," Nature Communications, vol. 4, Published Online May 14, 2013, 13 pages.
Liu, H. et al., "The newly established human liver cell line: a potential cell source for the bioartificial liver in the future," Human Cell, vol. 26, No. 4, Dec. 2013, Published Online Jun. 25, 2013, 7 pages
Marekova, D. et al., "Hepatocyte Growth on Polycapronolactone and 2-Hydroxyethylmethacrylate Nanofiber Sheets Enhanced by Bone Marrow-Derived Mesenchymal Stromal Cells," Hepato-Gastroenterology, vol. 60, No. 125, Jul. 2013, 8 pages.
Zhang, S. et al., "Integration of single-layer skin hollow fibers and scaffolds develops a three-dimensional hybrid bioreactor for bioartificial livers," Journal of Materials Science: Materials in Medicine, vol. 25, No. 1, Jan. 2014, Published Online Aug. 21, 2013, 10 pages.
Wikswo, J. et al., "Scaling and systems biology for integrating multiple organs-on-a-chip," Lab on a Chip, vol. 13, No. 18, Sep. 21, 2013, 31 pages.
Nelson, L. et al., "Profiling the Impact of Medium Formulation on Morphology and Functionality of Primary Hepatocytes in vitro," Scientific Reports, vol. 3, Sep. 24, 2013, 9 pages.
Wang, X. et al., "Therapeutic evaluation of a microbioartificial liver with recombinant HepG2 cells for rats with hepatic failure," Expert Opinion on Biological Therapy, vol. 13, No. 11, Nov. 2013, Published Online Sep. 27, 2013, 4 pages.
Ginai, M. et al., "The use of bioreactors as in vitro models in pharmaceutical research," Drug Discovery Today, vol. 18, No. 19-20, Oct. 2013, 14 pages.
Struecker, B. et al., "Liver support strategies: cutting-edge technologies," Nature Reviews: Gastroenterology & Hepatology, vol. 11, No. 3, Mar. 2014, Published Online Oct. 29, 2013, 11 pages.
Selden, C. et al., "Evaluation of Encapsulated Liver Cell Spheroids in a Fluidised-Bed Bioartificial Liver for Treatment of Ischaemic Acute Liver Failure in Pigs in a Translational Setting," PLoS ONE, vol. 8, No. 12, Dec. 18, 2013, 12 pages.
Smith, A. et al., "Microphysiological systems and low-cost microfluidic platform with analytics," Stem Cell Research & Therapy, vol. 4, Supp. 1, Dec. 20, 2013, 5 pages.
Nayak, S. et al., "Silk sericin-alginate-chitosan microcapsules: Hepatocytes encapsulation for enhanced cellular functions," International Journal of Biological Macromolecules, vol. 65, Apr. 2014, Published Online Jan. 28, 2014, 9 pages.
Sciancalepore, A. et al., "A Bioartificial Renal Tubule Device Embedding Human Renal Stem/Progenitor Cells," PLoS ONE, vol. 9, No. 1, Jan. 30, 2014, 11 pages.
Kutepov, D. et al., "The opportunities for extracorporeal treatment of hepatic failure," Khirurgiia, vol. 4, Feb. 4, 2014, 7 pages. (Submitted with Machine Translation of Article Abstract).
Malchesky, P., "Artificial Organs 2013: A Year in Review," Artificial Organs, vol. 38, No. 3, Mar. 2014, 30 pages.
Hilal-Alnaqbi, A. et al., "Effect of membranes on oxygen transfer rate and consumption within a newly developed three-compartment bioartificial liver device: Advanced experimental and theoretical studies," Biotechnology and Applied Biochemistry, vol. 61, No. 3, May 2014, Published Online Mar. 18, 2014, 12 pages.
Du, C. et al., "Induced pluripotent stem cell-derived hepatocytes and endothelial cells in multi-component hydrogel fibers for liver tissue engineering," Biomaterials, vol. 35, No. 23, Jul. 2014, Published Online Apr. 26, 2014, 9 pages.
Zhang, R. et al., "Identification of Proliferating Human Hepatic Cells From Human Induced Pluripotent Stem Cells," Transplantation Proceedings, vol. 46, No. 4, May 2014, 4 pages.
Chen, Y. et al., "Rapid Large-Scale Culturing of Microencapsulated Hepatocytes: A Promising Approach for Cell-Based Hepatic Support." Transplantation Proceedings, vol. 46, No. 5, Jun. 2014, 9 pages.
Vacanti, J. et al., "Liver cell therapy and tissue engineering for transplantation," Seminars in Pediatric Surgery, vol. 23, No. 3, Jun. 2014, 6 pages.
Sussman, N. et al., "Artificial Liver," Clinical Gastroenterology and Hepatology, vol. 12, No. 9, Sep. 2014, Published Online Jun. 6, 2014, 4 pages.

(56) References Cited

OTHER PUBLICATIONS

Yu, C. et al., "Evaluation of a novel choanoid fluidized bed bioreactor for future bioartificial livers," World Journal of Gastroenterology, vol. 20, No. 22, Jun. 14, 2014, 10 pages.

Hegde, M. et al., "Dynamic Interplay of Flow and Collagen Stabilizes Primary Hepatocytes Culture in a Microfluidic Platform," Lab on a Chip, vol. 14, No. 12, Jun. 21, 2014, 13 pages.

Noto, F. et al., "Aneuploidy is permissive for hepatocyte-like cell differentiation from human induced pluripotent stem cells," BMC Research Notes, vol. 7, Jul. 8, 2014, 9 pages.

Kamiya, A. et al., "Stem and progenitor cell systems in liver development and regeneration," Hepatology Research, vol. 45, No. 1, Jan. 2015, Published Online Jul. 18, 2014, 9 pages.

Kondo, Y. et al., "Histone Deacetylase Inhibitor Valproic Acid Promotes the Differentiation of Human Induced Pluripotent Stem Cells into Hepatocyte-Like Cells," PLoS ONE, vol. 9, No. 8, Aug. 1, 2014, 11 pages.

Zhang, R. et al., "Efficient Hepatic Differentiation of Human Induced Pluripotent Stem Cells in a Three-Dimensional Microscale Culture," Methods in Molecular Biology, vol. 1210, Aug. 6, 2014, 11 pages.

Esch, M. et al., "Body-on-a-Chip Simulation with Gastrointestinal Tract and Liver Tissues Suggests that Ingested Nanoparticles Have the Potential to Cause Liver Injury," Lab on a Chip, vol. 14, No. 16, Aug. 21, 2014, 25 pages.

Giri, S. et al., "Immortalization of Human Fetal Hepatocyte by Ectopic Expression of Human Telomerase Reverse Transcriptase, Human Papilloma Virus (E7) and Simian Virus 40 Large T (SV40 T) Antigen Towards Bioartificial Liver Support." Journal of Clinical and Experimental Hepatology, vol. 4, No. 3, Sep. 2014, 11 pages.

Yu, Y. et al., "Potential and Challenges of Induced Pluripotent Stem Cells in Liver Diseases Treatment," Journal of Clinical Medicine, vol. 3, No. 3, Sep. 2014, 20 pages.

Mobarra, N. et al., "Efficient Differentiation of Human Induced Pluripotent Stem Cell (hiPSC) Derived Hepatocyte-Like Cells on hMSCs Feeder," International Journal of Hemotology-Oncology and Stem Cell Research, vol. 8, No. 4, Oct. 1, 2014, 10 pages.

Baxter, M. et al., "Phenotypic and functional analyses show stem cell-derived hepatocyte-like cells better mimic fetal rather than adult hepatocytes," Journal of Hepatology, vol. 62, No. 3, Mar. 2015, Published Online Oct. 18, 2014, 9 pages.

Sarika, P. et al., "A non-adhesive hybrid scaffold from gelatin and gum Arabic as packed bed matrix for hepatocyte perfusion culture," Materials Science and Engineering C, vol. 46, Jan. 2015, Published Online Oct. 23, 2014, 7 pages.

Banares, R. et al., "Molecular Adsorbent Recirculating System and Bioartificial Devices for Liver Failure," Clinics in Liver Disease, vol. 18, No. 4, Nov. 2014, 12 pages.

Chien, Y. et al.,"Synergistic effects of carboxymethyl-hexanoyl chitosan, cationic polyurethane-short branch PEI in miR122 gene delivery: Accelerated differentiation of iPSCs into mature hepatocyte-like cells and improved stem cell therapy in a hepatic failure model," Acta Biomaterialia, vol. 13, Feb. 2015, Published Online Nov. 21, 2014, 17 pages.

ISA Korean Intellectual Property Office, International Search Report Issued in Application No. PCT/US2016/031911, dated Aug. 29, 2016, WIPO, 5 pages.

ISA Korean Intellectual Property Office, International Search Report and Written Opinion Issued in Application No. PCT/US2016/031911, dated Aug. 29, 2016, WIPO, 14 pages.

\* cited by examiner

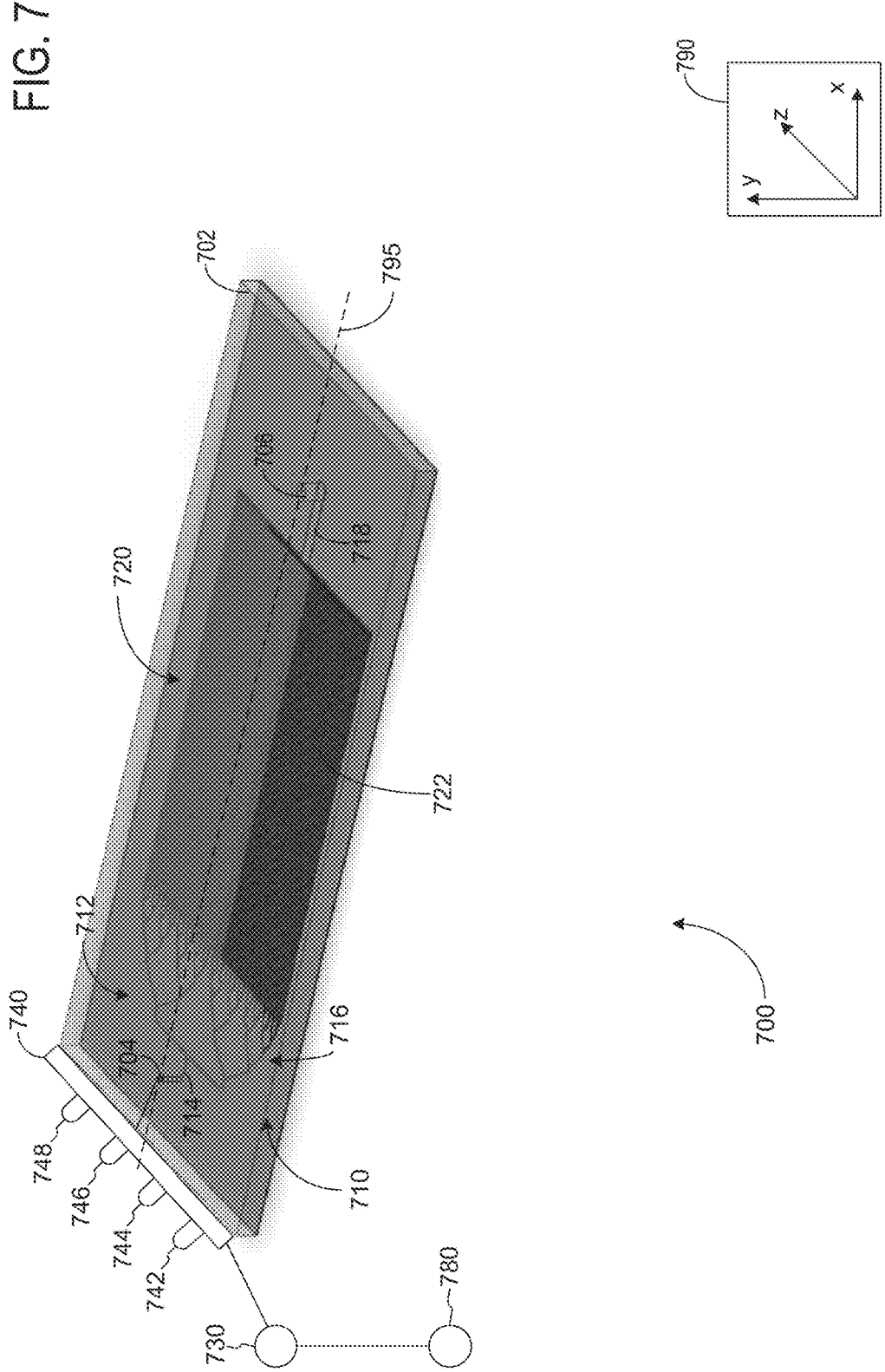

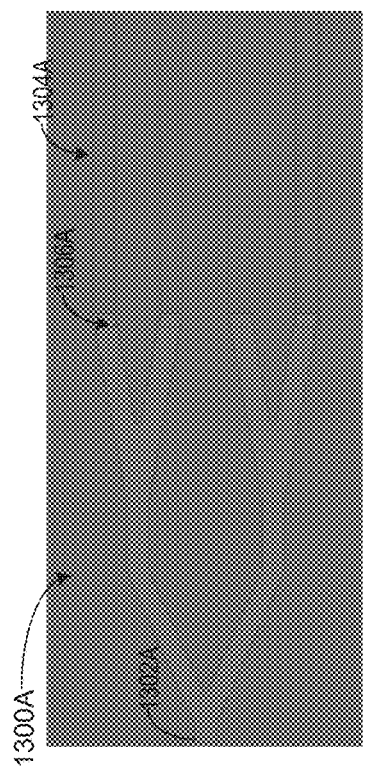
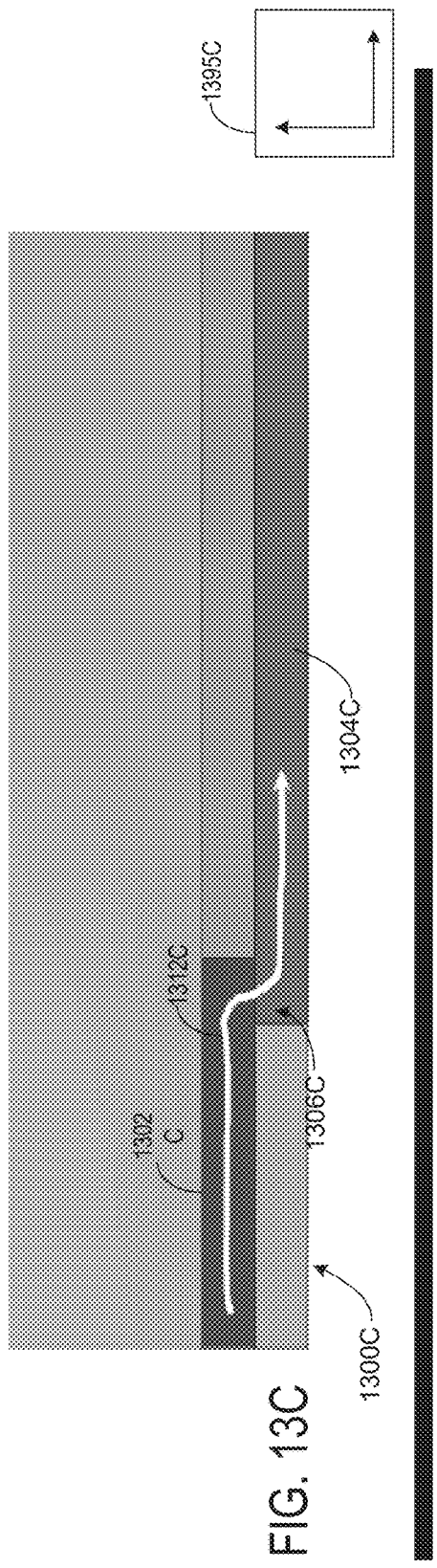
FIG. 13A  Inlet detail
FIG. 13B  Outlet detail
FIG. 13C  Cross section of header to channel transition

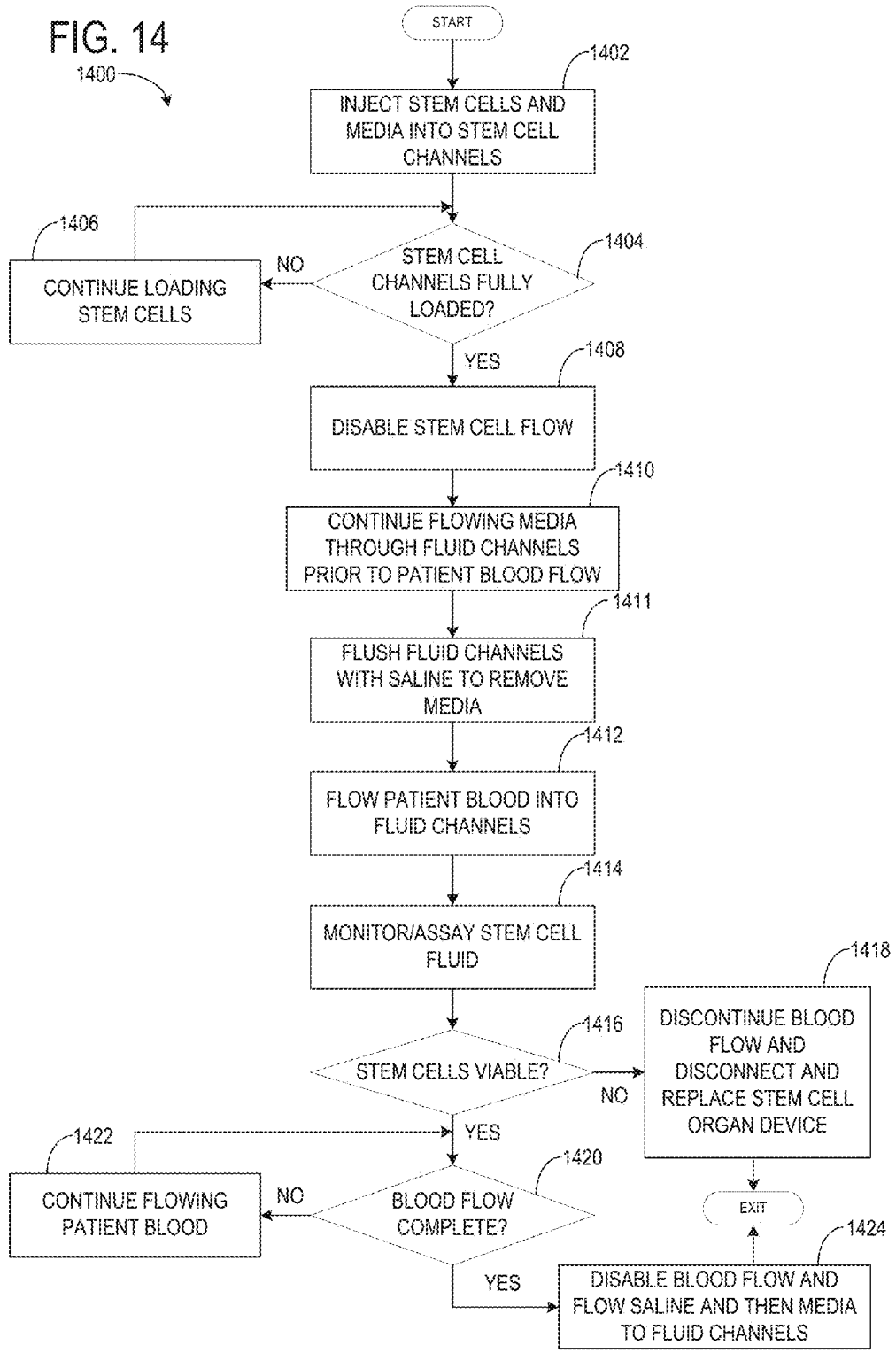

METHOD AND SYSTEM FOR A BIOARTIFICIAL ORGAN

CROSS REFERENCE TO RELATED APPLICATION

The present application claims priority to U.S. Provisional Patent Application No. 62/160,440, entitled "Method and System for a Bioartificial Organ," filed on May 12, 2015, the entire contents of which are hereby incorporated by reference for all purposes.

FIELD

The present description relates generally to methods and systems for a bioartificial organ for supporting a patient.

BACKGROUND/SUMMARY

Patients suffering from organ disease and/or failure rely on medical devices to perform the necessary organ functions for treatment of their organ disease and/or while awaiting organ transplant. Such medical devices may include membranes for transferring nutrients, chemicals, or the like, to a patient's bloodstream. In one example, bioreactor devices may be used to support patient's while awaiting organ transplant. Bioreactor devices may include hollow fiber membranes seeded with cells (e.g., cells of the required organ type) for performing organ functions and transferring toxins away from and/or nutrients to the patient's bloodstream. However, the inventors herein have recognized problems with such approaches. As one example, hollow fiber membranes may have issues with cell viability and longevity. As such, cells may die over time, thereby requiring the patient to be switched to a new device. Thus, these devices may not be effective as longer term support devices for patients. As another example, such devices may also have increased packaging space, thereby making the device larger and less portable.

As one example, the issues described above may be at least partially addressed by a stem cell organ device, comprising a first channel adapted to house a plurality of cells, a second channel, a membrane arranged between the first channel and the second channel, and a first inlet manifold coupled to the first channel. In one example, one or more interior surfaces of the first inlet manifold may include guides. As such, when cells are injected into the first channel, the cells may spread more evenly over and across the first channel, thereby increasing a transfer of molecules between the cells and blood flowing through the second channel during patient use.

It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

FIG. 7 shows perspective view of an assembled stem cell organ device with a variable pump.

FIGS. 13A-13C show a relationship between loading channels and channels of the channel layer of an embodiment of a stem cell organ device.

FIG. 14 illustrates a flow chart of a method for preparing and operating a stem cell organ device.

DETAILED DESCRIPTION

Figure 1:
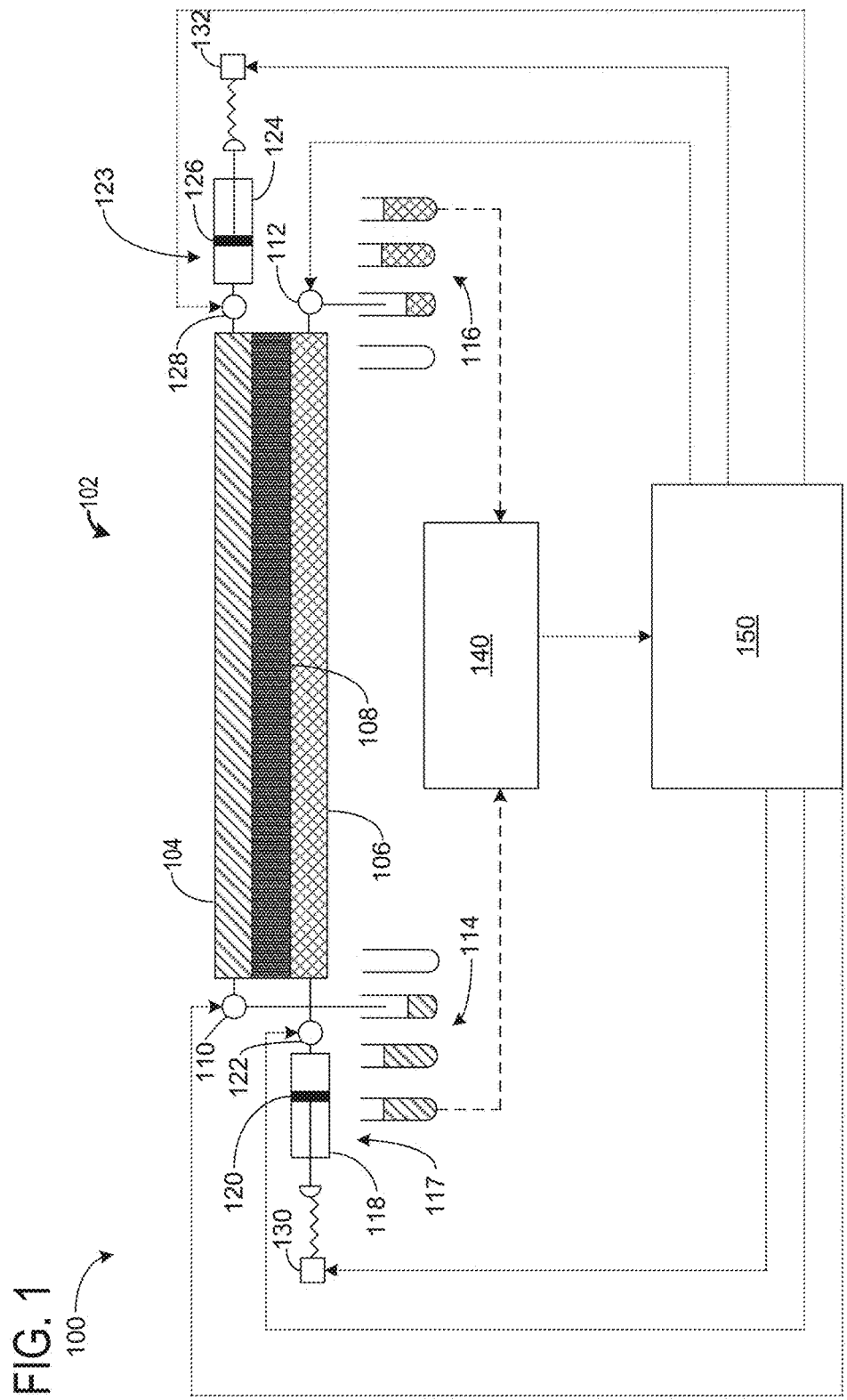
FIG. 1 illustrates a stem cell organ device and associated flow and sampling circuit.
Figure 2:
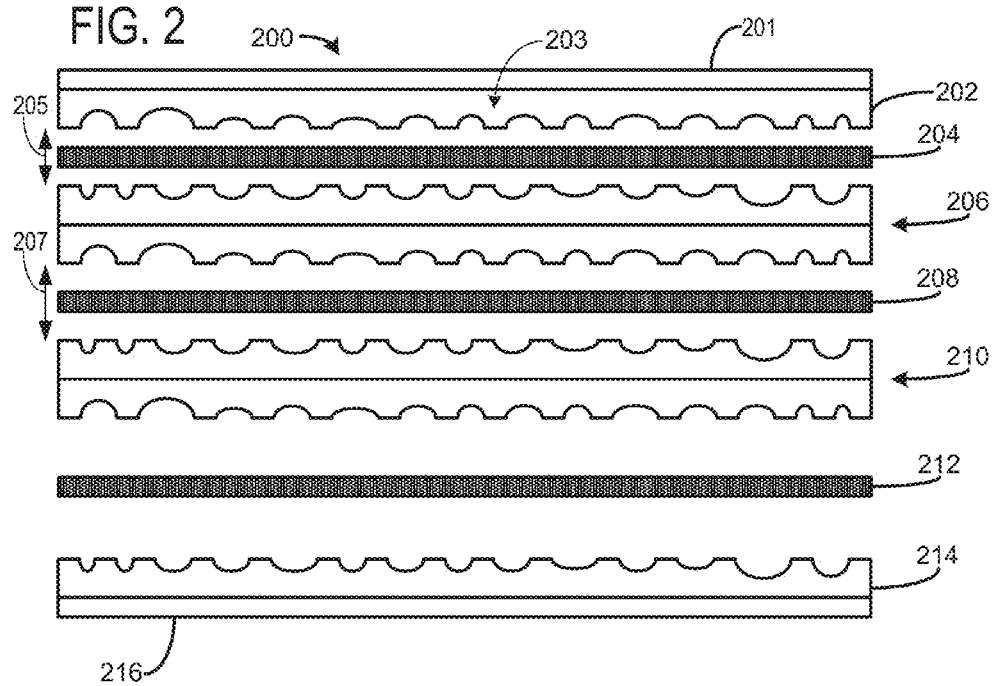
FIG. 2 illustrates an example structure of a plurality of microchannels used in a stem cell organ device.
Figure 3:
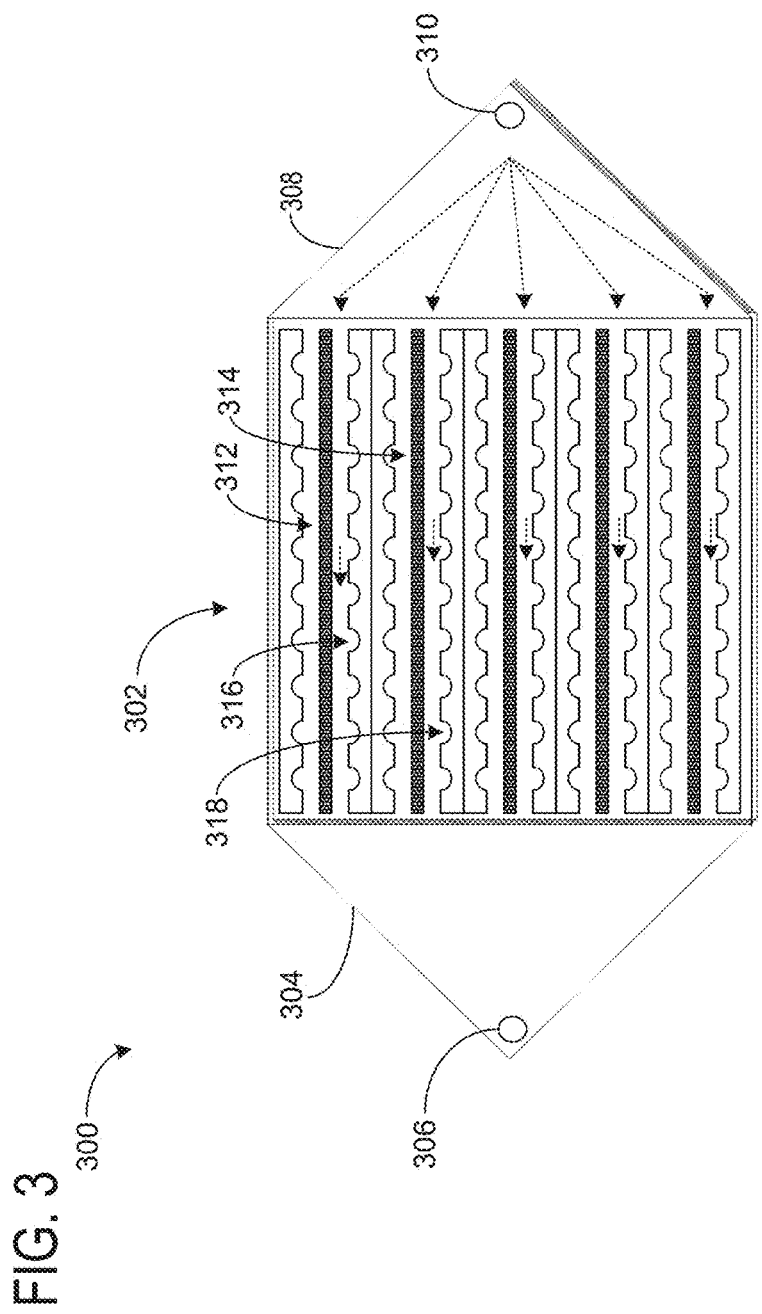
FIG. 3 illustrates an embodiment of a side view of a stem cell organ device.
Figure 4:
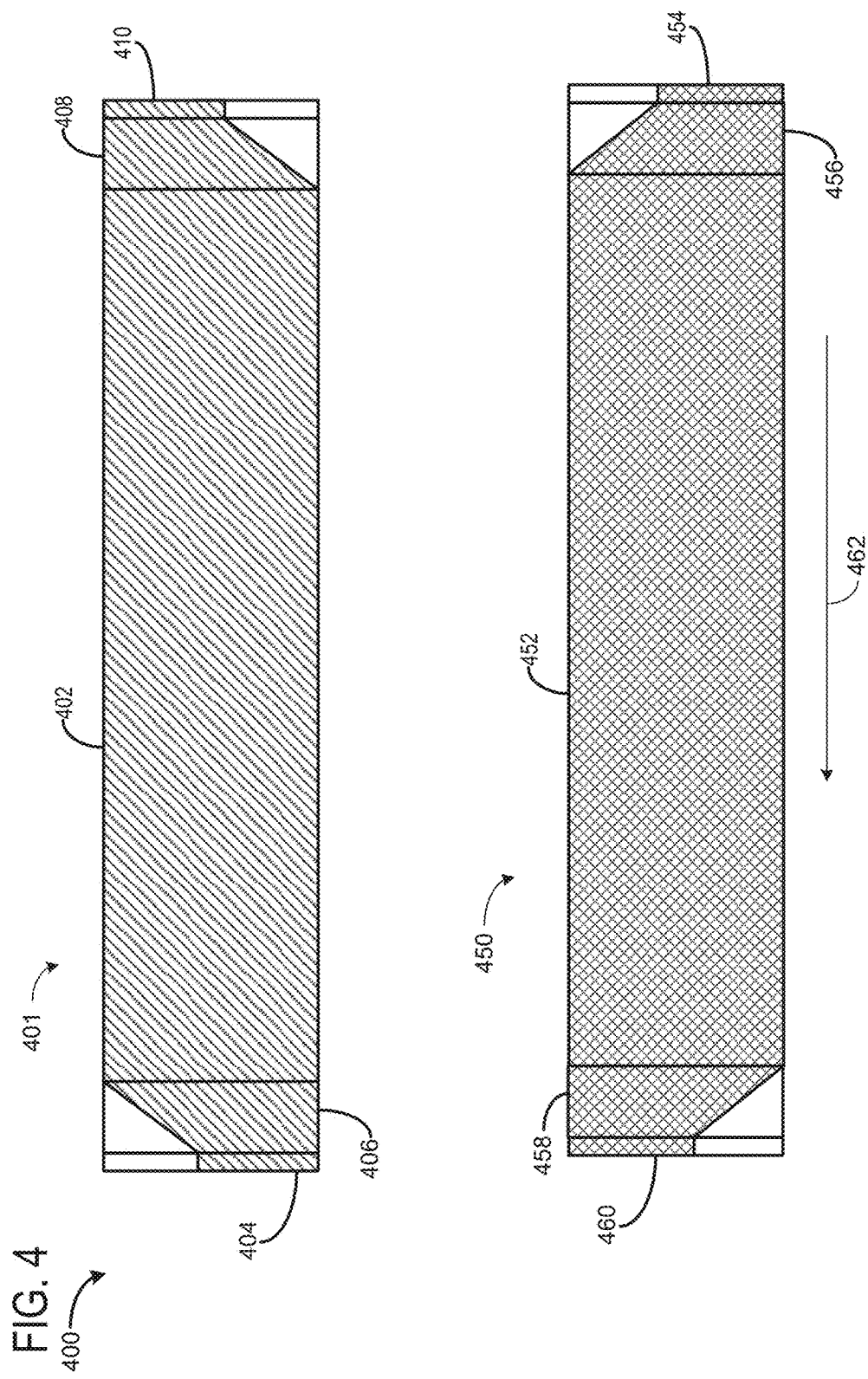
FIG. 4 illustrates a top-down view of a stem cell organ device including alternating stem cell channels and fluid channels comprising respective manifolds for receiving and releasing a flow of stem cells and blood.
Figure 5A:
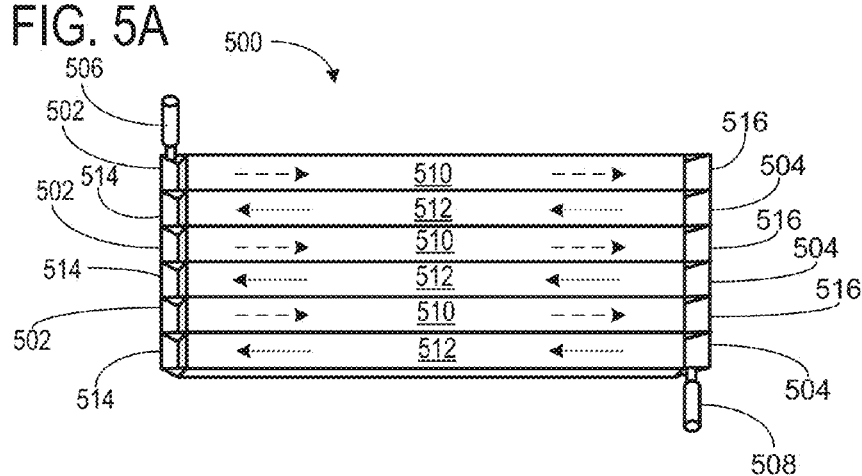
FIGS. 5A, 5B, and 5C illustrate a stem cell organ device with a stem cell manifold and a fluid manifold, an example of a single stem cell channel fluidly coupled to a portion of the stem cell manifold, and example flows of stem cells without guides and with guides within a stem cell channel.
Figure 5B:
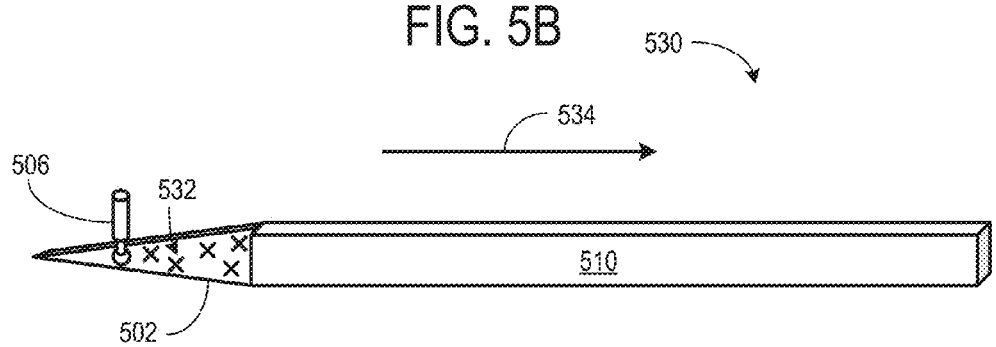
Figure 5C:
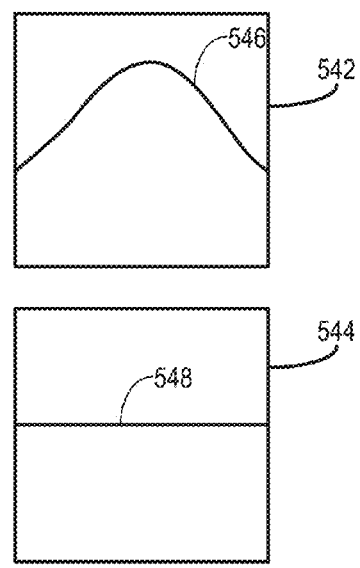
Figure 15:
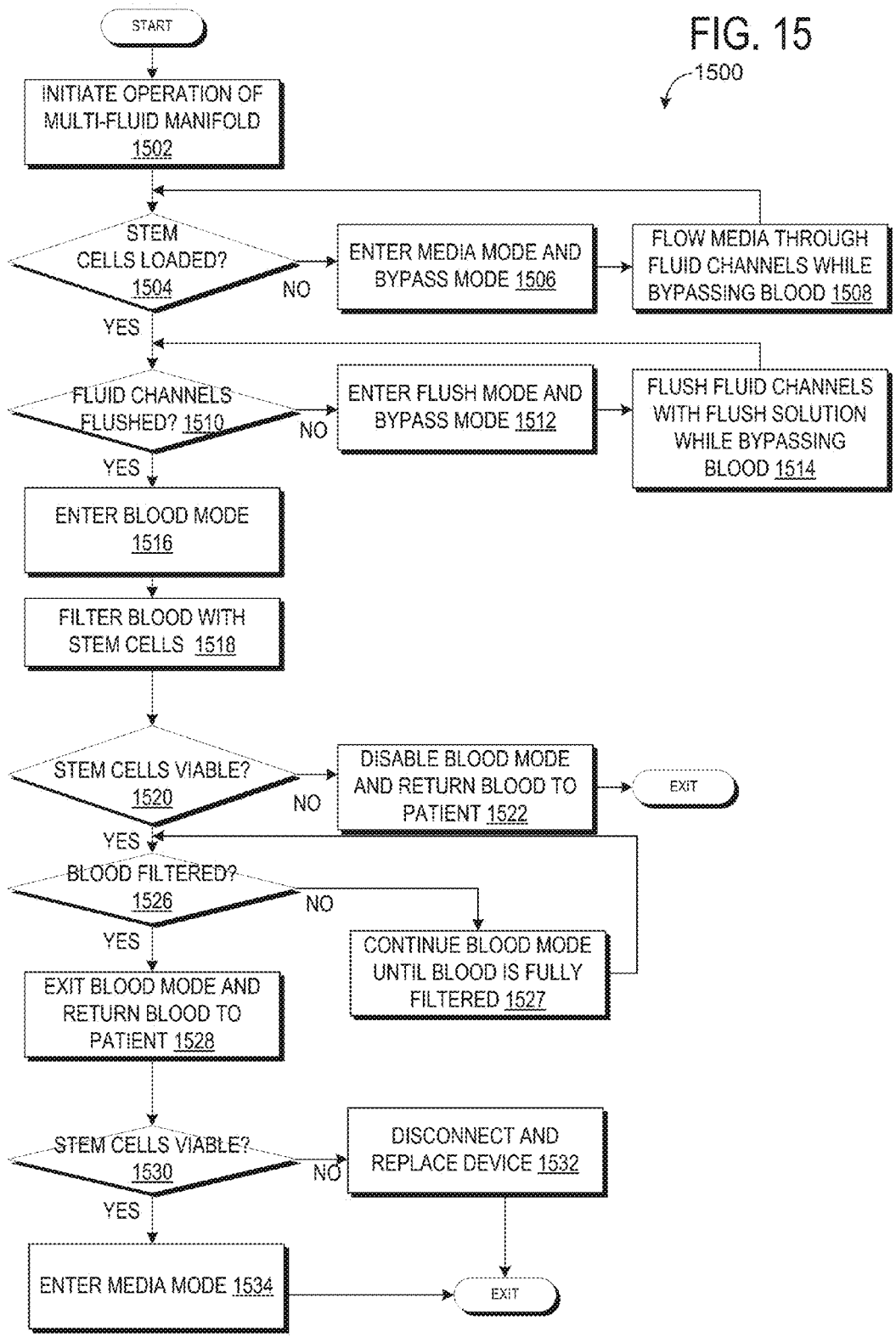
FIG. 15 shows a method for operating the stem cell organ device with the variable pump and multi-fluid manifold.
Figure 16:
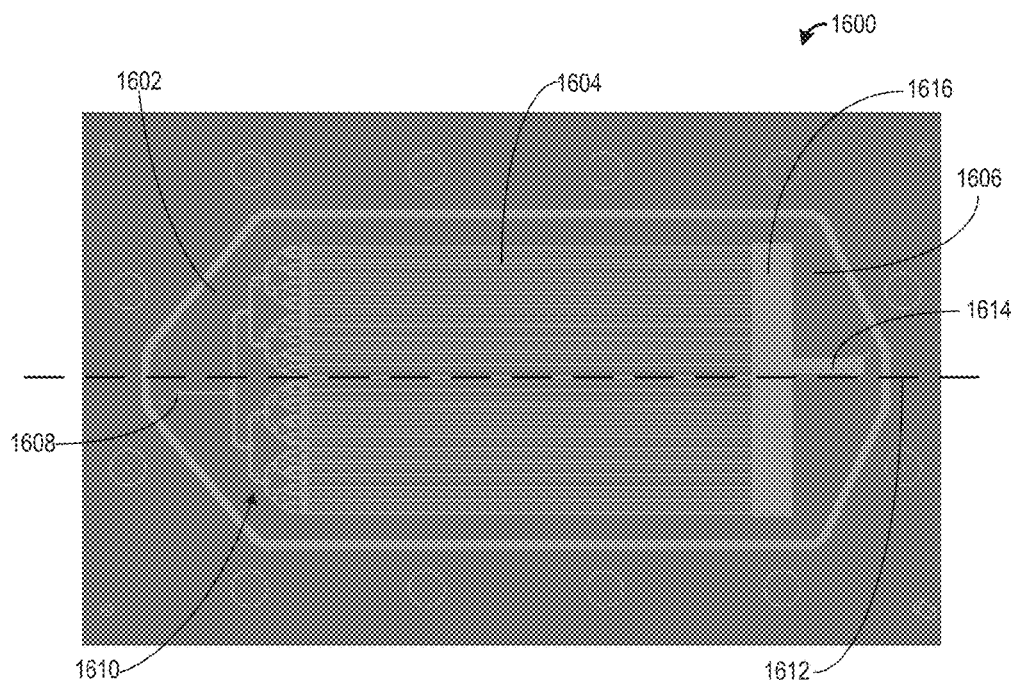
FIG. 16 shows a stem cell layer of another embodiment of a stem cell organ device.
Figure 17:
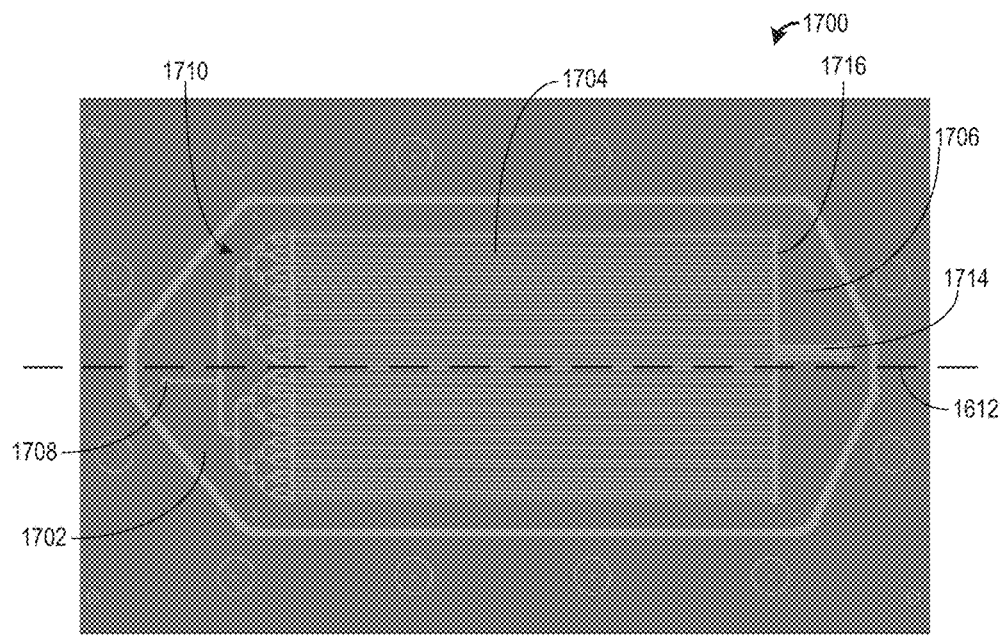
FIG. 17 shows a fluid layer of another embodiment of a stem cell organ device.
Figure 18:
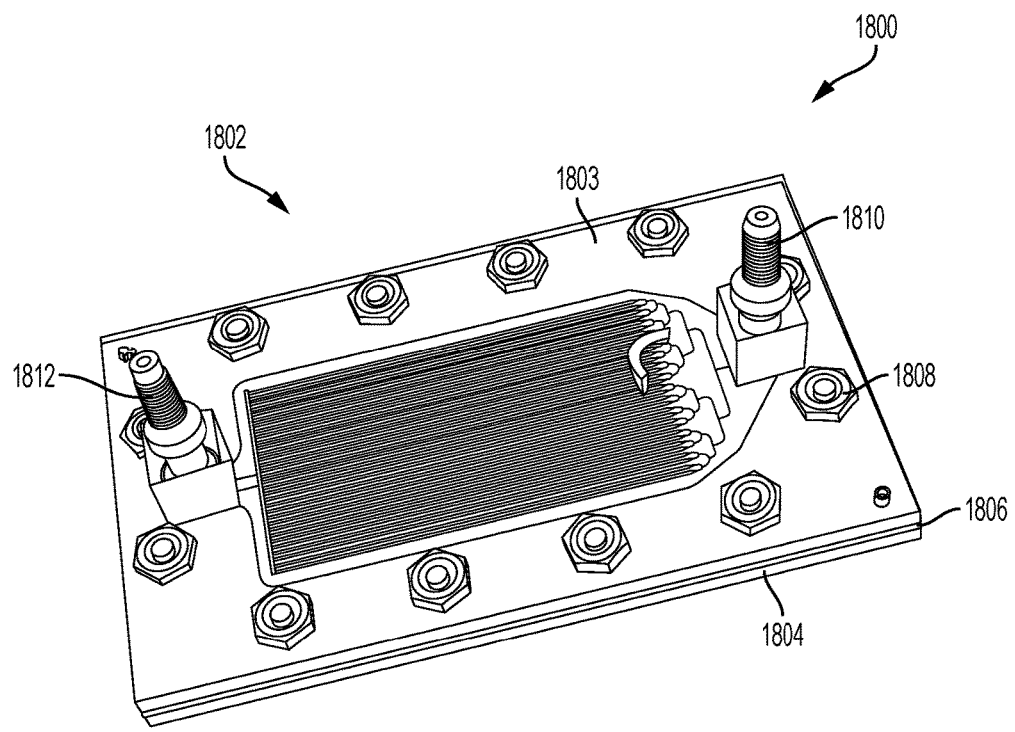
FIG. 18 shows a top perspective view of an assembled stem cell organ device.
Figure 19:
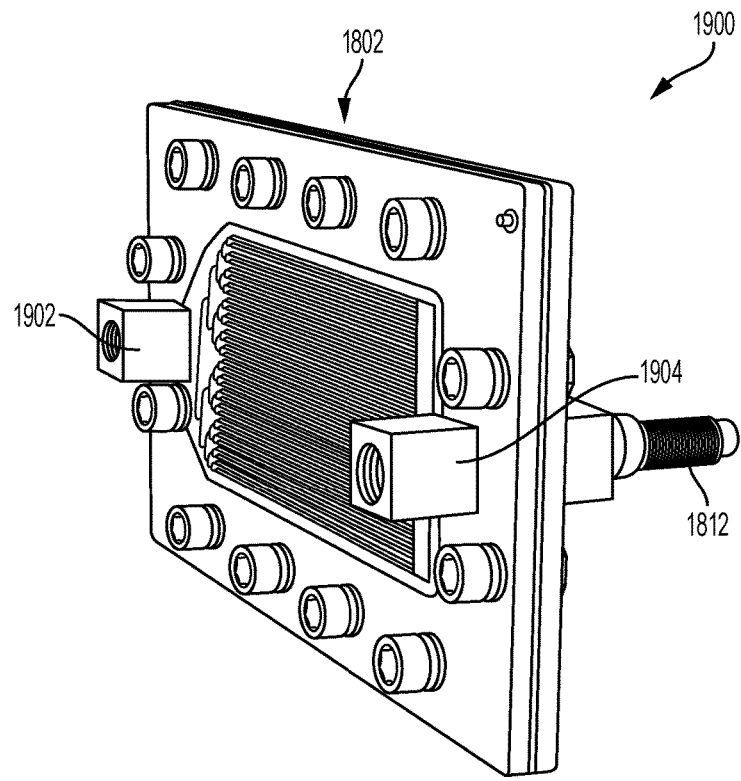
FIG. 19 shows a side perspective view of the assembled stem cell organ device of FIG. 18.
Figure 20:
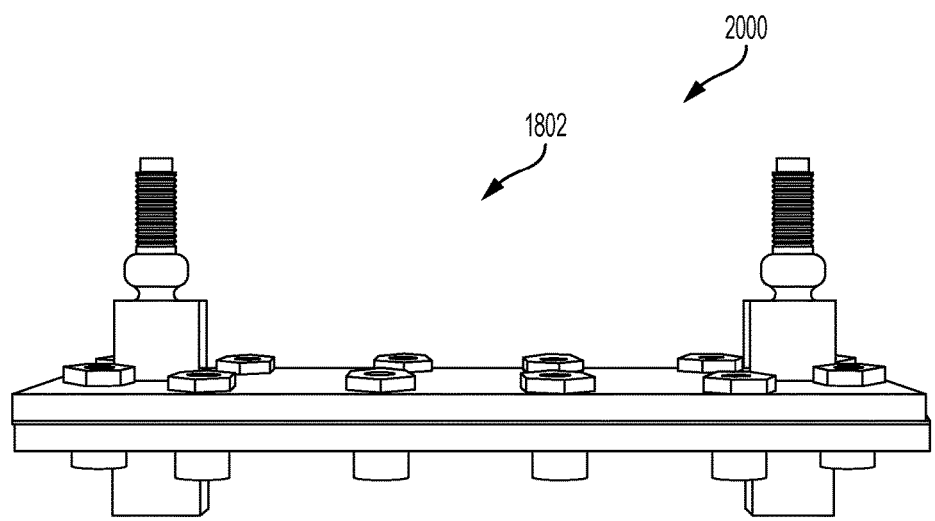
FIG. 20 shows a side view of the assembled stem cell organ device of FIGS. 18-19.
Figure 21:
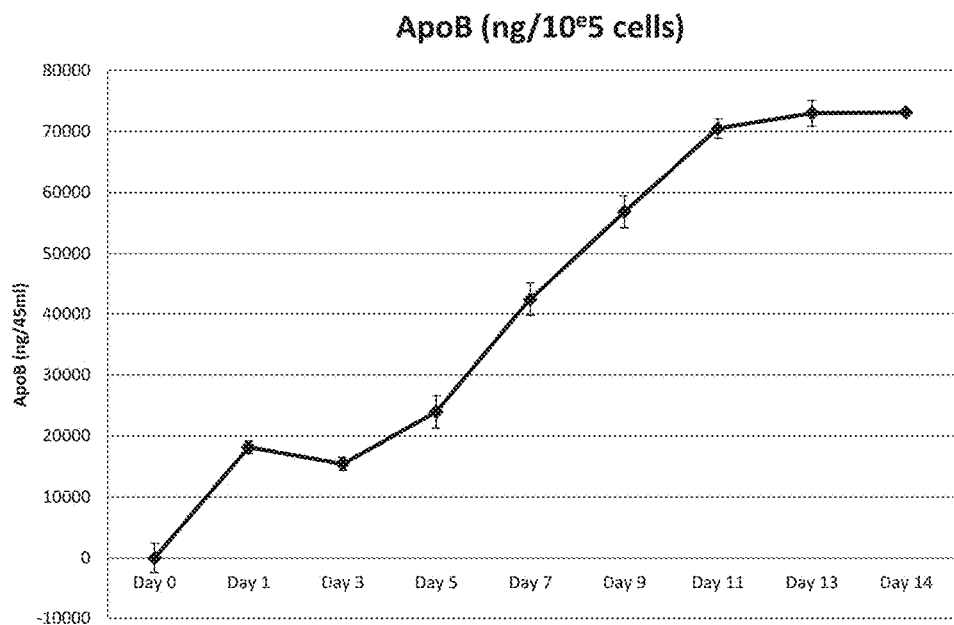
FIG. 21 shows a first graph of a first protein secreted by stem cells of a first stem cell organ test device over a period of 14 days.
Figure 22:
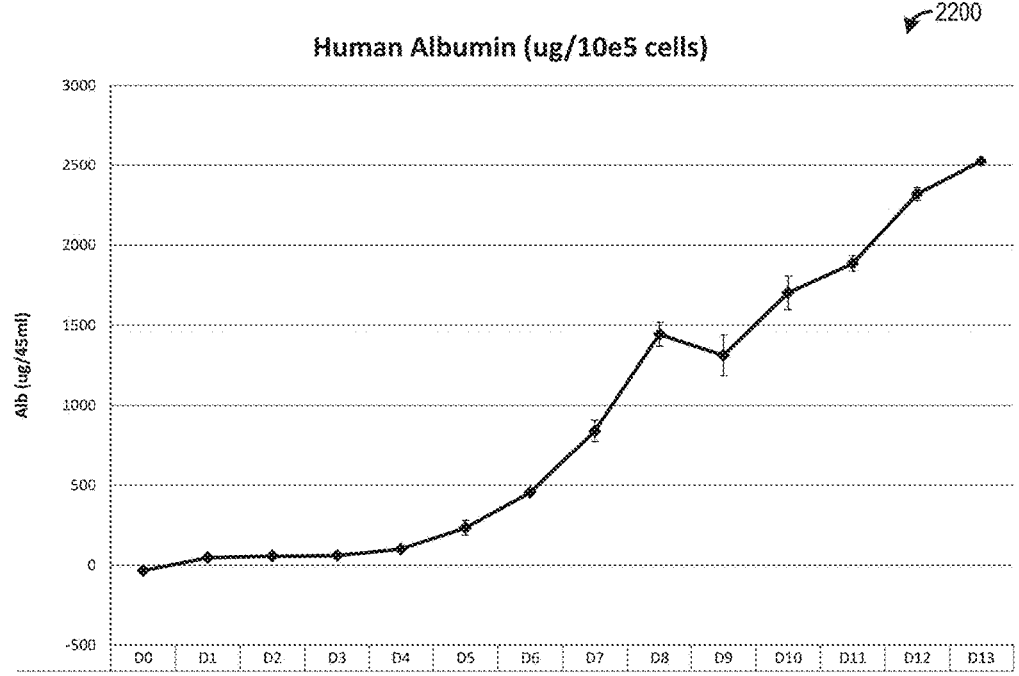
FIG. 22 shows a second graph of a second protein secreted by stem cells of the first stem cell organ test device over a period of 14 days.
Figure 23:
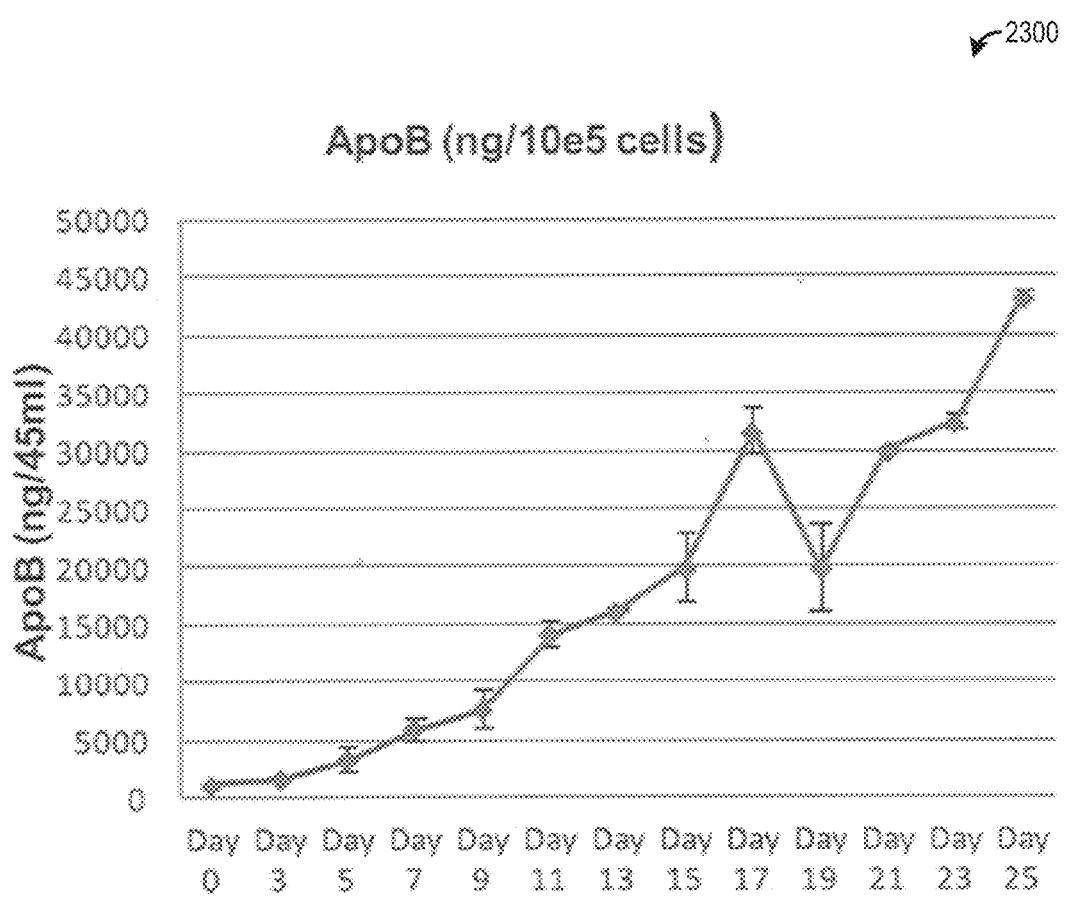
FIG. 23 shows a third graph of a first protein secreted by stem cells of a second stem cell organ test device over a period of 25 days.

The following description relates to systems and methods for operating a stem cell organ device including an array of alternating stem cell channels and fluid channels. The stem cell organ device may be located in a healthcare facility (hospital, clinic, ICU, etc.) and/or a portable device that allows a patient to use the device outside of a medical office (e.g., at work, at home, at a store, etc.). More specifically, the stem cell organ device may include at least one stem cell layer including a plurality of stem cell channels, at least one fluid layer including a plurality of fluid channels, and at least one membrane separating the stem cell layer and the fluid layer. During a first, stem cell loading period and media mode, stem cells (as well as media including nutrients) may be loaded into the plurality of stem cell channels and additional media including various nutrients may slowly flow through the plurality of fluid channels of the stem cell organ device. Once the device is ready for patient treatment (e.g., the loaded cells have affixed to the membrane and have grown to a threshold level), the fluid channels are flushed with a flushing solution to remove the media (such as saline). Blood from a patient may then be directed through the fluid channels during a treatment period. The stem cells and blood may be monitored via a HPLC or other cell assay device in order to determine a viability and/or performance of the cells, as shown in FIG. 1. FIGS. 2-6 show various embodiments of the stem cell organ device. In one embodiment, the stem cell channels and fluid channels each comprise ridges in order to allow a single layer of cells to flow through the respective channels, as shown in FIG. 2. A stem cell organ device with a first manifold and a second manifold is shown in FIG. 3. A top-down view of the stem cell organ device along with a view removing the stem cell channel such that the fluid channel is illustrated is shown in FIG. 4. A first pump coupled to a first manifold and a second pump coupled to a second manifold are shown along with a plurality of alternating stem cell and fluid channels in FIG. 5A. A single stem cell channel with an inlet manifold comprising guides is shown in FIG. 5B. Example flows with and without guides are shown in FIG. 5C. Various embodiments of guides of the stem cell organ device are shown in FIGS. 6A, 6B, 6C, 6D, 6E, and 6F. A top of the stem cell device including the fluid portion (or layer) is shown in FIG. 7. Layers of a first embodiment of a stem cell organ device, namely a stem cell loading layer, a stem cell channel layer, a membrane layer, a fluid channel layer, and a fluid loading layer are shown in FIGS. 8, 9, 10, 11, and 12 respectively. A relationship between loading channels and stem-cell channels is shown in FIGS. 13A-13C. A method for loading the stem cell channels with stem cells and operating the stem cell organ device with or without flowing blood is shown in FIG. 14. FIG. 15 shows a method for operating a blood pump of the stem cell organ device. A second embodiment of the stem cell organ device is shown in FIGS. 16-17. The second embodiment of the stem cell organ device includes at least one stem cell layer including stem cell channels connected between inlet and outlet stem cell manifolds (as shown in FIG. 16) and at least one fluid layer including fluid channels connected between inlet and outlet fluid manifolds (as shown in FIG. 17). The at least one stem cell layer and at least one fluid layer may be separated from one another via a membrane layer, such as the membrane layer shown in FIG. 10. FIGS. 18-20 show different views of an embodiment of an assembled stem cell organ device. In one example, the stem cell organ device of FIGS. 18-20 may include a single stem cell layer and a single fluid layer separated by a single membrane. In other embodiment, the stem cell organ device may include multiple stem cell, fluid, and membrane layers within the assembled stem cell organ device. FIGS. 21-23 show testing results from several stem cell organ test devices that were loaded with a plurality of stem cells. Over a period of 14-25 days, the stem cells were allowed to grow and affix to the membrane of the stem cell organ devices. The graphs of FIGS. 21-23 show protein secretion levels of the stem cells over the testing periods, thereby showing evidence of cell growth and viability. Thus, stem cells grown within the stem cell organ device may be used in a treatment mode to transfer nutrients and toxins to/from a patient's blood running through the fluid layer(s) of the stem cell organ device.

Turning now to FIG. 1, a system 100 comprising a stem cell organ device 102, a cell assay system (e.g., such as a high performance liquid chromatography (HPLC) system) 140, and a computer 150 is illustrated. In one example, the stem cell organ device 102 is a micro energy and chemical system (MECS) based stem cell organ device. The MECS based stem cell organ device is a microfluidic device including an array of parallel microchannels and may be referred to herein as a microchannel device. As depicted in FIG. 1, the stem cell organ device 102 comprises one stem cell channel 104 (represented by slanted lines) and one fluid channel 106 (represented by crisscross lines) separated by a membrane 108 (represented by a dotted box). However, in some embodiments, a plurality of stem cell channels, fluid channels, and membranes (e.g., filters) may exist, as shown in FIGS. 2-3, and thus the stem cell organ device 102 includes an array of alternating channels.

The stem cell channel 104 is adapted to hold various types of stem cells (e.g., stem cells for liver, pancreas, kidney, lung, etc.) to function as an external organ. The stem cells may be grown outside of the stem cell channel 104 and injected into the stem cell channel 104 via an injector 123. The fluid channel 106 is adapted to flow various fluids therein. For example, the fluid channel 106 may flow cell nutrients (also referred to herein as media) during a media mode (which may include a period of loading and/or growing cells), saline during a flushing mode (such as when transitioning between the media mode and a treatment or blood mode), and blood during a patient treatment mode (which includes transferring nutrients to the patient's bloodstream and toxin away from the patient's bloodstream via the stem cells). A membrane 108 is arranged between the fluid channel 106 and the stem cell channel 104. The membrane 108 prevents the flow of fluid between the fluid channel 106 and the stem cell channel 104. However, the membrane 108 does allow diffusion of smaller molecules (or ions) between the blood and stem cell channels, such as allowing the transfer of toxins from blood flowing through the fluid channel 106 to the cells loaded into the stem cell channel 104. The membrane 108 may also allow diffusion of molecules, such as ions, salts, nutrients, etc., from the cells in the stem cell channel 104 to the blood flowing through the fluid channel 106. The membrane 108 may prevent the diffusion of proteins from the fluid channel 106 to the stem cell channel 104. In one example, the membrane 108 may allow salt, water, and toxins (e.g., urea) to flow from the fluid channel 106 to the stem cell channel 104. As one example, the membrane 108 is a relatively flat sheet membrane including a variety of pores capable of exchanging certain-sized molecules or ions (e.g., molecules smaller than the pore size) between the blood or media flowing in the fluid channel 106 and the cells in the stem cell channel 104 without allowing diffusion of the stem cells into the fluid channel 106 or blood or media into the stem cell channel 104. The membrane 108 chemistries and porosities may be different based on a type of stem cell present in the stem cell channel 104 (e.g., kidney stem cells, liver stem cells, pancreas stem cells, etc.). Further, the membrane 108 may be a microporous membrane having pores with a diameter on the micro-scale. In this way, the membrane 108 is adapted for microfiltration between elements in the fluid channel 106 and elements in the stem cell channel 104. By including stem cells to perform filtering functions of a designated organ with a patient's bloodstream, the stem cell organ device 102 simulates functions of a corresponding organ (e.g., bioartificial organ).

The stem cells in the stem cell channel 104 may become saturated with toxins and/or degrade in function after a threshold duration of use (e.g., a threshold duration of flowing blood through the device, such as 12 hours, in one example). The threshold time may be adjusted based on a patient, the flow rate of blood through the device, and the composition of the blood flowing through the device. For example, a greater flow rate of blood through the fluid channel 106 may result in a decreased threshold duration of use (e.g., 8 hours). In order to ensure proper filtration of blood, the stem cells may be sampled via the HPLC 140 (or alternate cell assay system) via instructions from the computer 150 to open a stem cell pressure controller 110 and flow a metered amount of stem cells (e.g., 10-100 μL) into stem cell sample tubes 114. The stem cell pressure controller 110 is electrically coupled to and may receive instruction from the computer 150. Likewise, a corresponding sample of blood flowing through the fluid channel 106 may be sampled and injected into the HPLC 140 via instructions from the computer 150 to open a blood pressure controller 112 and flow a metered amount of blood (e.g., 10-100 μL) to blood sample tubes 116. A stem cell sample tube 114 may be sampled by the HPLC 140 and a corresponding blood sample tube 116 may be subsequently sampled by the HPLC 140. The HPLC 140 may provide information to the computer 150 regarding a concentration of compounds in the stem cell and the blood. For example, if a stem cell sample is measured to have a relatively low concentration of a first molecule by the HPLC 140, while a blood sample is measured to have a concentration of the first molecule (e.g., such as a toxin or molecule that is supposed to be transferred from the blood to the stem cells) is greater than a threshold (e.g., an amount of the first molecule that may be potentially harmful to a patient), then diffusion between the stem cell channel 104 and the fluid channel 106 may be below a desired diffusion rate. As another example, if a stem cell sample has a toxin level greater than a threshold stem cell toxin level (e.g., an amount of toxins in the stem cells where the desired diffusion rate may no longer be met), then the stem cells may need to be replaced due to degradation (e.g., decreased viability). As another example, if the stem cell sample has a threshold level of certain molecule, or a ratio of certain molecules within the sample is outside of a threshold range, decreased cell viability may be indicated. A portion of the stem cell organ device 102 may be at least partially transparent (e.g., clear) such that a user may visualize a state of the stem cells (e.g., such as the viability of the stem cells) in the stem cell channel 104 and visually determine if the stem cells are still viable (e.g., functional).

If the computer (e.g., electronic controller) 150 in communication with various sensors of the stem cell organ device (such as cell viability sensors, which may include the HPLC described above) determines that cell viability of the stem cells within the stem cell channel 104 is below a threshold level, the stem cell organ device 102 use may be terminated so that the stem cell organ device 102 may be recharged (e.g., reloaded) with new stem cells or new cell media to foster a nutrient rich environment for the stem cells to continue to be viable/functional or the stem cell organ device may be replaced with a new device containing viable stem cells. As such, the stem cell organ device 102 may include an additional blood, nutrient or flush solution pump or pumps for flowing cell media through the stem cell channel 104. In another example, the stem cell channel 104 may be coated with a material that contains the cell media and/or nutrients to increased stem cell viability.

If it is determined that the stems cells within the stem cell channel 104 need to be replaced, the degraded stem cells may first be removed, or flushed, from the stem cell channel 104. In order to replace degraded stem cells, the computer 150 signals a stem cell actuator 132 to actuate a plunger 126 of a syringe 124 to inject an amount of stem cells (e.g., new and viable stem cells) into the stem cell channel 104. The amount of stem cells may be based on an intended duration of operation of the stem cell organ device 102 or a difference between the toxin level in the stem cells and the threshold stem cell toxin level. For example, as the difference increases, the amount of stem cells injected also increases. The amount of stem cells injected may be controlled by one or more of a stem cell inlet pressure controller 128 and the stem cell actuator 132. The stem cell inlet pressure controller 128 is at least partially open when stem cells are injected into the stem cell channel 104 by the syringe 124.

The stem cells in the stem cell channel 104 are not continuously replaced. As one example, the stem cells remain in the stem cell channel 104 until a toxin level (e.g., a level of a molecule that indicates decreased cell viability) in the stem cell channel 104 exceeds the threshold stem cell toxin level. Therefore, the stem cell channel is only opened to the injector 123 and an inlet manifold of the stem cell channel (e.g., stem cell inlet manifold) during filling (or refilling) of the stem cell channel 104 with stem cells.

In an alternate embodiment, the stem cells may not be replaced within the stem cell organ device and instead the degraded device may be replaced with a different stem cell organ device containing viable stem cells.

In one embodiment, the fluid channel 106 may always be open during stem cell organ device 102 operation such that saline, cell media, or blood is always flowing through the fluid channel 106 via a pump 117 (e.g., such as a syringe pump, centripetal pump, or roller pump). For example, during a treatment period when blood flows through the device, unfiltered blood from a patient may flow in a first end of the fluid channel 106 via the pump 117, be filtered as it passes through the fluid channel 106, exits out of a second end of the fluid channel 106, and then returns to a patient's bloodstream within the patient. In one example, the computer 150 signals an actuator 130 to actuate a plunger 120 of the syringe 118 of the pump 117 to inject a volume of blood into the fluid channel 106. The volume of blood injected into the fluid channel 106 may be based on a rate of blood flowing out of the fluid channel 106 and into a patient (not shown). The volume of blood injected may be controlled by one or more of a blood inlet pressure controller 122 and the blood actuator 130 based on signals received from the computer 150. The plunger 120, syringe 118, and blood actuator 130 may form the pump 117, in one example.

In another embodiment, a multi-fluid variable pump may be used to inject saline, media, and blood into the stem cell organ device during operation (e.g., in a flushing phase, media phase, or treatment/blood phase of device operation). The multi-fluid variable pump may be electrically coupled to a controller with instructions for carrying out the operation. The controller may be an electronic controller containing non-transitory memory configured to store the instructions for carrying out operation of the multi-variable pump. For example, the controller may actuate various actuators of the variable pump in order to flow media (e.g., containing various cell nutrients), saline, or blood continuously through the fluid channel(s) of the stem cell organ device until a treatment period (e.g., filtering blood) is complete or the stem cells are no longer viable. As described above, cell viability may be determined via HPLC 140. As an example, additionally or alternatively, stem cell viability may be determined by an optical sensor. The optical sensor (e.g., a spectrophotometer) may measure a color, absorbance, and/or UV emittance. If the color changes (cells become darker), light absorbance changes (decreases), and/or UV emittance changes (decreases), then the cells may no longer be viable and operation of the stem cell organ device may be terminated. In one example, termination of the stem cell organ device includes one or more of disabling blood flow, removing the degraded stem cells, and washing the stem cells channels with saline or stem cell media (e.g., Luria broth, growth media, etc.). In another example, termination of the stem cell organ device includes one or more of disabling blood flow through the fluid channels, flushing the fluid channels with saline, and/or replacing the stem cell organ device with a new device containing stem cell channels with viable stem cells.

FIG. 1 depicts a system 100 for filtering blood in a fluid channel via stem cells in a stem cell channel via a membrane, where the membrane is disposed between the fluid channel and the stem cell channel. An example structure of the stem cell organ device 102, including a stem cell channel and a blood flow channel, will be described in greater detail below with respect to FIG. 2.

Turning now to FIG. 2, a system 200 depicts an array of microchannels, such as the fluid channel 106 and stem cell channel 104 shown in FIG. 1, of varying size. For example, a stem cell channel width may vary based on a type of stem cell loaded into the stem cell channel (e.g., 10-100 microns). In this way, the stem cell channel may comprise a single layer of stem cells. A top support plate 201 is in face-sharing contact with a top plate 202. A membrane 204 (e.g., similar to membrane 108 of FIG. 1) is located between the top plate 202 and a two sided plate 206. The two sided plate 206 and the top plate 202 comprise ridges 203. Stem cells may flow into and be loaded onto a space (e.g., channel) formed between the top plate 202 and the membrane 204 while blood may flow in a space (e.g., channel) formed between the membrane 204 and the two sided plate 206. The ridges 203 may be used to guide a stem cell or blood flow in a stem cell channel or a fluid channel, respectively. As depicted, the ridges 203 vary in size from a first ridge to a subsequent ridge. In some embodiments, additionally or alternatively, a size of the ridges of the top plate 202 may not be equal to a size of the corresponding ridges of the two sided plate 206 nearest the membrane 204. In another example, the ridges of the top plate 101 and a surface of the two-sided plate 206 facing the membrane 204 may be substantially equal. In this way, the top plate 202 and a first side of the membrane 204 may be in contact with stem cells while the portion of the two sided plate 206, nearest the membrane 204, and a second side of the membrane 204 may be in contact with blood.

A portion of the two sided plate 206 nearest a membrane 208 may be in contact with stem cells (e.g., the portion of the two sided plate 206 nearest the membrane 208 and the membrane 208 create a stem cell channel). The portion of the two sided plate 206 nearest the membrane 208 comprises ridges substantially equal to the ridges of the top plate 202. In this way, ridges in contact with stem cells may be substantially equal in shape and size. A portion of a two sided plate 210 nearest the membrane 208 (e.g., the portion of the two sided plate 210 nearest the membrane 208 and the membrane 208 create a fluid channel) may be in contact with blood, or another fluid flowing through the fluid channel. The ridges of the portion of the two sided plate nearest the membrane 208 may be substantially equal to the ridges of the portion of the two sided plate 206 nearest the membrane 204. In this way, ridges in contact with blood (or saline or media) may be substantially equal in shape and size.

A distance 205 between the top plate 202 and the portion of the two sided plate 206 nearest the membrane 204 may be less than a distance 207 between the portion of the two sided plate 206 nearest the membrane 208 and the portion of the two sided plate 210 nearest the membrane 208. In this way, a width of the stem cell channel and the fluid channel may be altered along the system 200. Thus, the array of microchannels may have differing widths.

Stem cells may lie between the membrane 212 and a surface of the two sided plate 210 facing the membrane 212. Blood may lie between the membrane 212 and a bottom plate 214. The bottom plate 214 is in face-sharing contact with a bottom support plate 216. The bottom plate 214 and the portion of the two sided plate 210 nearest the membrane 212 comprise ridges substantially similar to ridges in a fluid channel and a stem cell channel, respectively.

In some embodiments, the distance 205 may be substantially equal for all microchannels in a stem cell organ device include an array (e.g., plurality) of microchannels. Additionally or alternatively, the ridges of the microchannels may all be equal in size and shape (e.g., a first ridge of a stem cell channel may be substantially equal to a second ridge of the stem cell channel).

FIG. 2 depicts an example structure of a plurality of stem cell channels and fluid channels of an example stem cell organ device with ridges to help guide flow within the channel. FIG. 3 illustrates another example of a stem cell organ device including a plurality of microchannels of similar type to the channels shown in FIGS. 1 and 2.

Turning now to FIG. 3, a side-on view of a stem cell organ device 300 comprising a plurality of microchannels 302 (e.g., an array of microchannels, also referred to as a microchannel array or system) is depicted. The microchannels 302 are depicted as being evenly spaced apart and comprising ridges substantially equal to adjacent ridges of a same channel. For example, ridges in a first stem cell channel 312 are substantially equal to ridges in a second stem cell channel 314 in both size and shape. Furthermore, ridges in a first fluid channel 316 are substantially equal to ridges in a second fluid channel 318 in both size and shape. Ridges in stem cell channels may not be equal to ridges in fluid channels. Alternatively, ridges in the stem cell channels may be substantially equal to ridges in fluid channels in both size and shape. The stem cell organ device 300 may be an example of the stem cell organ device 102 of FIG. 1 and thus may function similarly as described above.

The stem cell organ device 300 further comprises a stem cell manifold 304 with a stem cell supply port 306. Likewise, on an opposite side of the stem cell organ device 300, there lies a fluid manifold 308 with a fluid injection port 310. Dashed arrows indicate a fluid flow direction (e.g., of blood, saline, or media) through the stem cell organ device 300.

The stem cell manifold 304 is fluidly coupled to only the stem cell channels of the stem cell organ device 300. Likewise, the fluid manifold 308 is fluidly coupled to only the fluid channels of the stem cell organ device 300. The stem cell supply port 306 may house a first pumping mechanism (e.g., syringe 124). The fluid supply port 310 may house a second pump mechanism (e.g., pump mechanism 118).

Turning now to FIG. 4, a top-down view of a stem cell channel 402 and a fluid channel 452 of a stem cell organ device 400 are depicted. The stem cell organ device 400 may be the same as the stem cell organ device 300 of FIG. 3 and/or the stem cell organ device 102 of FIG. 1. Slanted lines depict an area where stem cells may be present within the stem cell organ device 400. Criss-cross lines depict an area where fluid (such as blood) may be present within the stem cell organ device. The first view 401 of FIG. 4 shows a top view of the device where the stem cell channel 402 is positioned on top of a fluid channel and thus only the stem cell channel 402 is shown. The second view 450 of FIG. 4 shows a top view of the device where the stem cell channel 402 has been removed so the fluid channel 452 is uncovered and may viewed.

The stem cell channel 402 is fluidly coupled to a stem cell manifold 404 via a stem cell manifold pathway 406. A stem cell injection, or flow of stem cells, may occur at the stem cell manifold 404 and stem cells may flow through the stem cell manifold pathway 406 to the stem cell channel 402 and other stem cell channels (e.g., the additional stem cells located below the stem cell channel 402). For example, when loading the stem cell organ device 400 with stem cells, stem cells are injected via a port in the stem cell manifold 404 and stem cells may then flow through the stem cell manifold pathway 406 and through the stem cell channel 402 and the other stem cell channels in order to load each of the stem cell channels of the stem cell organ device 400 with stem cells, prior to patient use. The stem cell manifold 404 and/or the stem cell manifold pathway 406 may comprise guides to assist in evenly distributing the stem cells to a plurality of stem cell channels of the stem cell organ device 400. The guides will be discussed in greater detail below.

During device loading, stem cells may flow out of stem cell channel 402 via a stem cell outlet manifold pathway 408 leading to a stem cell outlet manifold 410. The stem cell outlet manifold 410 is on an opposite side of the stem cell organ device 400 compared to the stem cell inlet manifold 402. The stem cell channel 402 may further comprise a sieve for capturing stem cells during stem cell loading while allowing a bulk fluid to pass through the sieve and exit the stem cell channel 402. More specifically, an end of the stem cell channel 402 coupled to the stem cell outlet manifold pathway 408 may include the sieve positioned across an exit from the stem cell channel 402 to the stem cell outlet manifold pathway 408. In one example, the sieve may include a solid barrier including a plurality of apertures, where a diameter of each of the apertures is smaller than a diameter of the cells. The bulk fluid may be a mixture of fluid and nutrients used to grow the stem cells (referred to herein as cell media). The sieve may be removed during removal of degraded stem cells and then re-introduced during stem cell loading.

The fluid channel 452 is fluidly coupled to a fluid inlet manifold 454 via a fluid inlet manifold pathway 456. The fluid inlet manifold 454 and the fluid inlet manifold pathway 456 are fluidly coupled to only the fluid channel 452 and other fluid channels of the stem cell organ device 400. Fluid (such as blood, saline, or media) leaving the fluid channel 452 exits through a fluid outlet manifold pathway 458 to a fluid outlet manifold 460. Arrow 462 depicts a fluid (e.g., blood) flow direction through the fluid channel 452, fluid inlet manifold 454 and fluid outlet manifold 460.

The fluid inlet manifold 454 lies directly below the stem cell outlet manifold 410. Likewise, the fluid outlet manifold 460 lies directly below the stem cell inlet manifold 404. For a stem cell organ device with a plurality of alternating stem cell channels and fluid channels, the stem cell inlet manifold and fluid outlet manifold may also alternate corresponding to the alternating pattern of the stem cell channels and the fluid channels. Likewise the stem cell outlet manifold and the fluid inlet manifold may also alternate corresponding to the alternating pattern of the stem cell channels and the fluid channels. The stem cell inlet manifold, stem cell outlet manifold, fluid inlet manifold, and fluid outlet manifold will be discussed in greater detail below.

FIG. 4 depicts a top-down view of a stem cell organ device with a stem cell channel and a fluid channel comprising respective manifolds for receiving and releasing (or flowing) stem cells or fluid (e.g., blood, saline, or media), respectively. FIG. 5A depicts a side-on view of a stem cell organ device with alternating stem cell and fluid manifolds.

Turning now to FIG. 5A, a stem cell organ device 500 is shown, the stem cell organ device 500 comprising a plurality of stem cell inlet manifolds 502 and a plurality of fluid outlet manifolds 514 on a first side of the stem cell organ device and a plurality of fluid inlet manifolds 504 and a plurality of stem cell outlet manifolds 516 on a second side of the stem cell organ device 500, opposite the first side. The stem cell organ device 500 further comprises a plurality of stem cell channels 510 and a plurality of fluid channels 512, the plurality of stem cell channels 510 and plurality of fluid channels 512 alternating with one another such that each stem cell channel 510 is separated from other stem cell channels 510 by a fluid channel 512. The stem cell organ device 500 may be used as and operate similarly to the stem cell organ device 102 of FIG. 1.

Larger dashed arrows in the stem cell channels 510 represent a direction of stem cell flow when the stem cell organ device 500 is being loaded with stem cells before patient use. Smaller dashed arrows in the fluid channels 512 represent a direction of fluid flow when the stem cell organ device 500 is in use. The larger dashed arrows are greater in size than the smaller dashed arrows.

As one example, each of the stem cell inlet manifolds 502 are fluidly coupled to one another through a stem cell inlet connecting channel connected to each stem cell inlet manifold 502. All of the stem cell inlet manifold 502 and the stem cell inlet connecting channel may form one stem cell inlet manifold unit. As such, when stem cells are injected via a stem cell injector (as explained further below) into a first stem cell inlet manifold 502 (e.g., the top or outer stem cell inlet manifold 502), stem cells may flow between all of the fluidly connected stem cell inlet manifolds 502 and through all of the stem cell channels 510. In an alternate embodiment, each of the stem cell inlet manifolds 502 may be coupled to its own stem cell injector and stem cells may be injected individually into each stem cell inlet manifold 502 and the corresponding stem cell channel 510. Similarly, each of the stem cell outlet manifolds 516, each of the fluid inlet manifolds 504, and each of the fluid outlet manifolds 514 and corresponding connecting channels may form a stem cell outlet manifold unit, a fluid inlet manifold unit, and a fluid outlet manifold unit, respectively.

Each stem cell inlet manifold 502 is fluidly coupled to only stem cell channel 510 and not fluid channels 512. Further, each stem cell inlet manifold 502 is physically coupled to only one stem cell channel 510. The stem cell channels 510 are also fluidly coupled to the stem cell outlet manifolds 516. Each fluid inlet manifold 504 is fluidly coupled to only fluid channels 512. Further, each fluid inlet manifold 504 is physically coupled to only one fluid channel 512. The fluid channels 512 are also fluidly coupled to the fluid outlet manifolds 514. As depicted, the stem cell channels 510 and the fluid channels 512 alternate. Thus, the stem cell inlet manifolds 502 and the fluid outlet manifolds 514 alternate on the first side of the stem cell organ device 500 in order to align with the stem cell channels 510 and the fluid channels 512. Likewise, the fluid inlet manifolds 504 and the stem cell outlet manifolds 516 alternate on the second side of the stem cell organ device 500 in order to align with the fluid channels 512 and the stem cell channels 510. In this way, fluid may only flow from the fluid inlet manifolds 504, through the fluid channels 512, and into the fluid outlet manifolds 514, without mixing with stem cells. Likewise, the stem cells may only flow from the stem cell inlet manifolds 502, through the stem cell channels 510, and into the stem cell outlet manifolds 516, without crossing over to the fluid channels 512 (e.g., due to a membrane separating the fluid channels and stem cell channels, such as the membranes shown in FIGS. 1-3).

In an alternate embodiment, the stem cell inlet manifolds may be arranged on a same side of the stem cell organ device as the fluid inlet manifolds and the stem cell outlet manifolds may be arranged on a same side of the stem cell organ device as the fluid outlet manifolds. In this way, a loading direction of stem cells into the stem cell channels may be the same as a flow direction of fluid (e.g., blood, saline, or media) through the fluid channels.

A cross-section of each manifold of the stem cell inlet manifolds 502, fluid inlet manifolds 504, fluid outlet manifolds 514, and stem cell inlet manifolds 516 yields a triangular structure. Therefore, the manifolds 502, 504, 514, and 516 are shaped as triangular prisms. However, in alternate embodiments, alternate shapes are possible.

As described above, during a treatment mode when the stem cell organ device is connected to a patient, blood from the patient is continuously delivered to the fluid inlet manifolds 504, the fluid channels 512, and the fluid outlet manifolds 514 in order to transfer molecules and/or ions to/from the blood, and perform other blood filtering operations, before the filtered (e.g., treated) blood is returned to the patient. A rate of blood entering the fluid channels 512 may be equal to a rate of blood exiting the fluid channels 512. In this way, a volume of blood in the fluid channel 512 is kept relatively constant. In one example, a pump upstream or downstream of the stem cell organ device 500 may continuously pump blood from the patient and through the stem cell organ device 500.

As described above, stem cells are not continuously fed to the stem cell channels 510. Stem cells are loaded into the stem cell channels 510 prior to device use in the treatment mode and then the stem cells remain in the stem cell channels 510 until the stem cells become degraded (e.g., until viability of the stem cells reduces below a threshold level). The degradation (or level of viability) may be measured by a cell assay, such as a cell assay performed by HPLC system, measuring a level of certain molecules indicating low cell viability in the stem cells being greater than a threshold. In another example, cell viability may be determined by a user visualizing the stem cell degradation (e.g., degradation may cause discoloration, size change, shape change, cloudiness, etc.). Upon determination of degradation, the stem cell channels 510 may be opened to the stem cell inlet manifold 502 and to the stem cell outlet manifold 516. The degraded stem cells may be flushed out of the stem cell channels 510 and then new stem cells may be flown into the stem cell channels 510 to reload the device. During a stem cell loading procedure, a flow of stem cells into the stem cell channels 510 may be equal to a flow of stem cells out of the stem cell channel 510. The stem cells may flow through the stem cell channels 510 in a single layer.

A stem cell injector 506 is fluidly coupled to the stem cell inlet manifold 502, as described above with respect to FIG. 1. A flow of stem cells from the stem cell injector 506 is perpendicular to a flow of stem cells in the stem cell channels 510. Likewise, in one example, a flow of blood from a blood injector 508 (or blood pump coupled to the manifold) is perpendicular to a flow of blood in the fluid channels 512.

Turning now to FIG. 5B, a top-down representation 530 of an individual stem cell channel 510 is depicted. The stem cell channel 510 comprises a stem cell inlet manifold 502 and a stem cell injector 506, as described above. The stem cell inlet manifold 502 comprises guides 532. The guides 532 may be located on one or more inner surfaces of the stem cell inlet manifold 502. For example, the guides 532 may be on one or more of a bottom, inner surface, a top, inner surface, and side, inner surfaces of the stem cell inlet manifold 502. The guides 532 help guide the stem cells to flow uniformly into and through the stem cell channel 510 such that a coating of the stem cell channel 510 is even. Arrow 534 represents a direction of flow for the stem cells after injection and into the stem cell channel 510.

FIG. 5C depicts a first example flow 542 of stem cells through the stem cell channels without guides in the stem cell inlet manifold and a second example flow 544 of stem cells through the stem cell channels with guides in the stem cell inlet manifold. The first example flow 542 resembles a laminar flow of stem cells through the stem cell channel that has a parabolic shape. For example, laminar flow in a pipe (e.g., channel) results in a parabolic flow profile where the velocity of flow varies from zero at the walls of the channel to a maximum along the cross-sectional center of the channel. As depicted, a flow front 546 is curved due to the flow being laminar and unguided. The laminar flow profile may result in uneven distribution of stem cells in the stem cell channel. Uneven distribution of stem cells may lead to decreased molecular exchange between the blood and stem cells during device use (e.g., a rate of exchange is less than a threshold rate). Furthermore, the laminar flow profile has an uneven pressure across its flow front. For example, a pressure along the cross-sectional center of the channel is greater than a pressure along the walls of the channel. In this way, stem cells flowing along the cross-sectional center of the channel may be damaged upon reaching an end of the channel due to the greater pressure.

The second example flow 544 resembles a plug flow of stem cells through the stem cell channel, or uniform flow distribution across a cross-section of the stem cell channel. As depicted, a flow front 548 of the plug flow is relatively linear across the channel. The plug flow profile may evenly distribute stem cells to and along the stem cell channel due to the flow being guided by the guides in the inlet manifold coupled to the stem cell channel. The guides may aid in decreasing the surface tension of the stem cell inlet manifold, thereby more evenly distributing the flow of stem cells across the cross-section of the stem cell channel. Furthermore, a pressure of the flow of stem cells is even from the wall of the stem cell channel to a cross-sectional center of the stem cell channel. In this way, the stem cell channel may be more quickly and evenly loaded with guides compared to the loading without guides described above.

FIGS. 5A, 5B, and 5C illustrate alternating stem cell manifold and fluid manifolds fluidly coupled to alternating stem cell channels and fluid channels, respectively. The stem cell inlet manifolds may comprise guides to help evenly distribute stem cells in their corresponding channels. FIGS. 6A, 6B, 6C, 6D, 6E, and 6F depict various inner surfaces of the stem cell inlet manifold. As described above, the inlet manifolds resembles triangular prisms. Therefore, a top, bottom, or side inner surface of the inlet manifolds yields a triangle, as depicted in FIGS. 6A-6F.

Figure 6A:
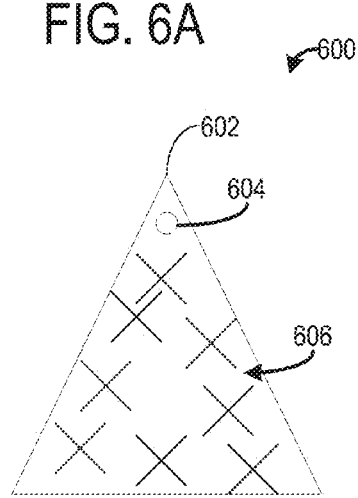
FIGS. 6A, 6B, 6C, 6D, 6E, and 6F illustrate example guides for the manifolds of the stem cell organ device.

Turning now to FIG. 6A, an embodiment 600 comprising an inner surface of a stem cell inlet manifold 602 comprising a stem cell injection port 604 is depicted. Thus, the embodiment 600 may show a top inner surface of a stem cell inlet manifold 602. However, a bottom or side inner surface of the inlet manifold 602 may include similar guides as shown for the top surface. As described above, the stem cell inlet manifold 602 flows stem cells to stem cell channels of a stem cell organ device.

The embodiment 600 further depicts the inner surface of the stem cell inlet manifold 602 with a plurality of guides 606. The guides are interspersed along the inner surface of the stem cell inlet manifold 602 such that there are regions of the inner surface of the stem cell inlet manifold 602 comprising guides 606 and remaining regions that do not comprise guides 606. In this way, the regions that do not comprise guides 606 separate the regions comprising guides 606 from one another. As depicted in the embodiment 602, the guides may be asymmetric and/or unorganized. The guides 616 may be laser etchings, protrusions, grooves, ingots, stamps, and/or other suitable alterations to the inner surface of the stem cell inlet manifold 602 such that the loading of stem cells into the stem cell channel is more uniform. The guides 606 may cross over one another such that they are perpendicular. Additionally or alternatively, the guides may include one or more sections of parallel lines, crisscrossing lines, overlapping lines, circles, swirls, and overlapping curved lines distributed either evenly or unevenly over a surface of the one or more interior surfaces.

Figure 6B:
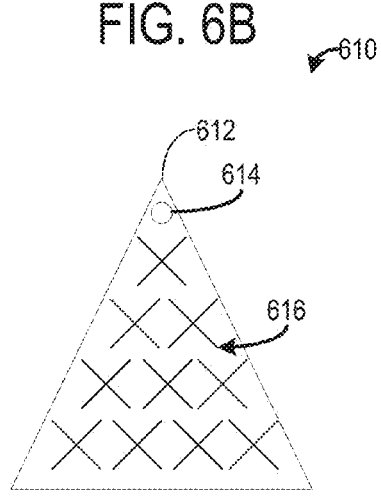

Turning now to FIG. 6B, an embodiment 610 comprising an inner surface of a stem cell inlet manifold 612 comprising a stem cell injection port 614 is depicted. Thus, the embodiment 610 may show a top inner surface of a stem cell inlet manifold 612. However, a bottom or side inner surface of the inlet manifold 612 may include similar guides as shown for the top surface. As described above, the stem cell inlet manifold 612 flows stem cells to stem cell channels of a stem cell organ device.

The embodiment 610 further depicts the inner surface of the stem cell inlet manifold 612 with a plurality of guides 616. The guides are interspersed along the inner surface of the stem cell inlet manifold 612 such that there are regions of the inner surface of the stem cell inlet manifold 612 comprising guides 616 and remaining regions that do not comprise guides 616. In this way, the regions that do not comprise guides 616 separate the regions comprising guides 606 from one another. As depicted in the embodiment 612, the guides may be symmetric and/or organized. The guides 616 may be laser etchings, protrusions, grooves, ingots, stamps, and other suitable alterations to the inner surface of the stem cell inlet manifold 612 such that the loading of stem cells into the stem cell channel is uniform. As depicted, the guides 616 may cross over one another such that they are perpendicular.

Figure 6C:
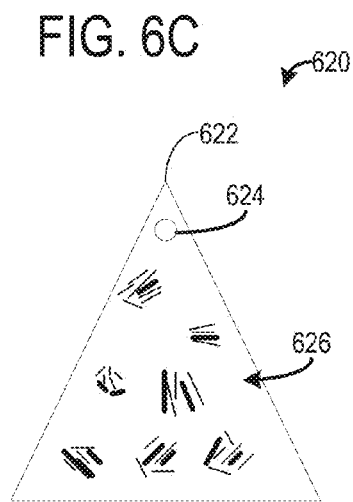

Turning now to FIG. 6C, an embodiment 620 comprising an inner surface of a stem cell inlet manifold 622 comprising a stem cell injection port 624 is depicted. Thus, the embodiment 620 may show a top inner surface of a stem cell inlet manifold 622. However, a bottom or side inner surface of the inlet manifold 622 may include similar guides as shown for the top surface. As described above, the stem cell inlet manifold 622 flows stem cells to stem cell channels of a stem cell organ device.

The embodiment 620 further depicts the inner surface of the stem cell inlet manifold 622 with a plurality of guides 626. The guides are interspersed along the inner surface of the stem cell inlet manifold 622 such that there are regions of the inner surface of the stem cell inlet manifold 622 comprising guides 626 and remaining regions that do not comprise guides 626. In this way, the regions that do not comprise guides 626 separate the regions comprising guides 626 from one another. The guides 626 may be laser etchings, protrusions, grooves, ingots, stamps, and other suitable alterations to the inner surface of the stem cell inlet manifold 622 such that the loading of stem cells into the stem cell channel is uniform. As depicted, the guides 626 may be linear and of a varying thickness. The guides 626 may be angled and overlapping one another. The guides 626 may be angled toward or parallel with a stem cell flow direction of stem cells being loaded into stem cell channels. Additionally or alternatively, the guides 626 may vary in size and length.

Figure 6D:
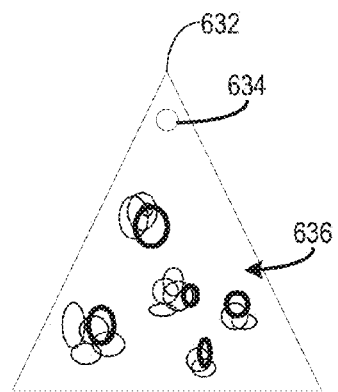

Turning now to FIG. 6D, an embodiment 630 comprising an inner surface of a stem cell inlet manifold 632 comprising a stem cell injection port 634 is depicted. Thus, the embodiment 630 may show a top inner surface of a stem cell inlet manifold 632. However, a bottom or side inner surface of the inlet manifold 632 may include similar guides as shown for the top surface. As described above, the stem cell inlet manifold 632 flows stem cells to stem cell channels of a stem cell organ device.

The embodiment 630 further depicts the inner surface of the stem cell inlet manifold 632 with a plurality of guides 636. The guides are interspersed along the inner surface of the stem cell inlet manifold 632 such that there are regions of the inner surface of the stem cell inlet manifold 632 comprising guides 636 and remaining regions that do not comprise guides 636. In this way, the regions that do not comprise guides 636 separate the regions comprising guides 636 from one another. The guides 636 may be laser etchings, protrusions, grooves, ingots, stamps, and other suitable alterations to the inner surface of the stem cell inlet manifold 632 such that the loading of stem cells into the stem cell channel is uniform. As depicted, the guides 636 may be circular or elliptical. The guides 636 may vary in thickness. The guides 636 may be angled to and overlapping one another. Additionally or alternatively, the guides 636 may vary in size and length.

Figure 6E:
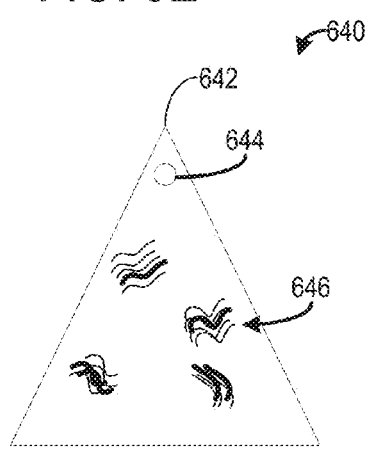

Turning now to FIG. 6E, an embodiment 640 comprising an inner surface of a stem cell inlet manifold 642 comprising a stem cell injection port 644 is depicted. Thus, the embodiment 640 may show a top inner surface of a stem cell inlet manifold 642. However, a bottom or side inner surface of the inlet manifold 642 may include similar guides as shown for the top surface. As described above, the stem cell inlet manifold 642 flows stem cells to stem cell channels of a stem cell organ device.

The embodiment 640 further depicts the inner surface of the stem cell inlet manifold 642 with a plurality of guides 646. The guides are interspersed along the inner surface of the stem cell inlet manifold 642 such that there are regions of the inner surface of the stem cell inlet manifold 642 comprising guides 646 and remaining regions that do not comprise guides 646. In this way, the regions that do not comprise guides 646 separate the regions comprising guides 646 from one another. The guides 646 may be laser etchings, protrusions, grooves, ingots, stamps, and other suitable alterations to the inner surface of the stem cell inlet manifold 642 such that the loading of stem cells into the stem cell channel is uniform. As depicted, the guides 646 may be wavy or straight. The guides 646 may vary in thickness. The guides 646 may be angled to and overlapping one another. Additionally or alternatively, the guides 646 may vary in size and length.

Figure 6F:
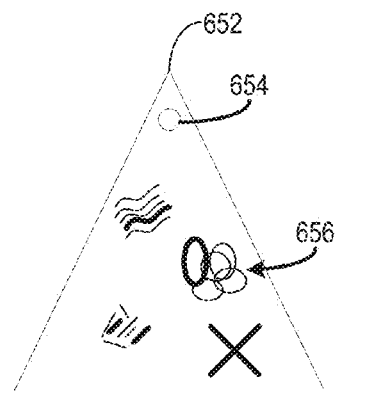

Turning now to FIG. 6F, an embodiment 650 comprising an inner surface of a stem cell inlet manifold 652 comprising a stem cell injection port 654 is depicted. Thus, the embodiment 650 may show a top inner surface of a stem cell inlet manifold 652. However, a bottom or side inner surface of the inlet manifold 652 may include similar guides as shown for the top surface. As described above, the stem cell inlet manifold 652 flows stem cells to stem cell channels of a stem cell organ device.

The embodiment 650 further depicts the inner surface of the stem cell inlet manifold 652 with a plurality of guides 656. The guides are interspersed along the inner surface of the stem cell inlet manifold 652 such that there are regions of the inner surface of the stem cell inlet manifold 652 comprising guides 656 and remaining regions that do not comprise guides 656. In this way, the regions that do not comprise guides 656 separate the regions comprising guides 656 from one another. The guides 656 may be laser etchings, protrusions, grooves, ingots, stamps, and other suitable alterations to the inner surface of the stem cell inlet manifold 652 such that the loading of stem cells into the stem cell channel is uniform. As depicted, the guides 656 may be mixture of guides 616 of FIG. 6B, guides 626 of FIG. 6C, guides 636 of FIG. 6D, and guides 646 of FIG. 6E. Although now depicted, the guides 656 may overlap with other guides of a dissimilar shape. For example, circular regions of the guides 656 may overlap with wavy regions of the guides 656. The guides 646 may vary in thickness. The guides 656 may be angled to and overlapping one another. Additionally or alternatively, the guides 656 may vary in size and length.

In some embodiments, additionally or alternatively, a first guide (e.g., circular guides) may be located on the bottom inner surface of the stem cell inlet manifold while a different guides (e.g., linear guides) may be located on the top inner surface of the stem cell inlet based on a type of stem cell loaded into the stem cell channel. For example, a stem cell inlet manifold for kidney stem cells may be substantially equal to or unequal to a stem cell inlet manifold for liver stem cells.

FIGS. 6A-6F depict various guides located along a stem cell inlet manifold to be used for uniformly loading stem cells in a stem cell channel. FIG. 7 depicts an embodiment of an assembled stem cell organ device.

Specifically, FIG. 7 shows a perspective view of a stem cell organ device 700. In the current view, only the fluid inlet and outlet manifolds are visible. The stem cell organ device 700 may be used similarly to any of the stem cell devices described herein. The stem cell organ device 700 may be compatible with one or more of a kidney, liver, pancreas, lung, etc. stem cells in one example. In another example, the stem cell channels stem cell organ device 700 may be compatible with only one of the kidney, liver, pancreas, lung, etc. stem cells based on a stem cell channel size. As described above, the stem cell channels are configured to allow stem cells to flow in a single file in order to increase transfer between the stem cells and a patient's blood. The stem cell organ device 700 does not use dialysate.

An axis system 790 comprises three axes, an x-axis parallel to the horizontal direction, a y-axis parallel to the vertical direction, and a z-axis perpendicular to both the x and y axes. A central axis 795 of the stem cell organ device is shown by a dashed line.

The stem cell organ device 700 comprises a glass cover layer 702, a loading layer 710, and a channel layer 720. The glass cover 702 is vertically higher than the loading layer 710 which is vertically higher than the channel layer 720. The above three layers depict a fluid portion of the stem cell organ device 700. Thus, in the current embodiment, the fluid portion is vertically higher than a stem cell portion and a membrane separating the stem cell and blood portions. A case (not shown) may be used to house the above components during operation.

The glass cover 702 is transparent and in face-sharing contact to the loading layer 710. Liquid and gas may flow between the glass cover 702 and the loading layer 710. An optical sensor or a patient may look through the glass cover 702 to visibly determine a state of the stem cells (e.g., viable or degraded). The glass cover 702 may be thicker than the loading layer 710 and the channel layer 720. The glass cover 702 may hermetically seal along an outer edge with the loading layer 710 such that fluid may not flow to an ambient atmosphere.

The loading layer 710 comprises an inlet header 712 with a series of bifurcating channels 716 fluidly coupled to an inlet 714 at a single passage. An inlet 704 extends downward from an outer surface of the glass layer 702 to the inlet 714. The bifurcating channels 716 lead to the fluid channels 722 of the channel layer 720.

The stem cell layer positioned below the fluid layer may include similar bifurcating channels that may comprise any of the above described etchings with respect to FIGS. 6A, 6B, 6C, 6D, 6E, and 6F. This allows the bifurcating channels to decrease laminar flow and evenly load the stem cell channels. Uneven flow may lead to bubbles or uneven filling of the stem cell channels, thereby reducing blood filtering during a stem cell device operation.

A number of fluid channels 722 (and similarly, stem cell channels) may be equal to a number of bifurcating channels 716. The fluid channels 722 align with the bifurcating channels 716 along the x and y axes. A direction of fluid flow to the fluid channels 722 and/or stem cell flow to the stem cell channels is described below with reference to FIGS. 13A-13C.

An outlet 706 is located on an opposite side of the stem cell organ device 700 compared to the inlet 704. The outlet 706 and inlet 704 are aligned along the central axis 795. However, in alternate embodiments, the outlet 706 and inlet 704 may be offset from one another relative to the central axis 795. The outlet 706 is larger than the inlet 704 in one example. The fluid channels 722 are fluidly coupled to the outlet 706 by an outlet passage 718. The fluid channels 722 may converge proximal to the outlet passage 718 such a single outflow of fluid may flow from the channel layer 720 to the outlet passage 718.

A pump 730 is electrically coupled to a controller 780, wherein the controller 780 comprises computer-readable instructions for actuating various actuators of the pump 730 based on one or more of a type or size of stem cell device, stem cell type, blood conditions, etc. The conditions are further described below with respect to FIG. 15. In some embodiments, the pump and the controller may be combined into a single device such that the pump houses the controller in order to reduce a profile of the stem cell organ device 700. The pump 730 is coupled to a manifold 740 comprising four ports, namely a flush port 742, a media port 744, a blood port 746, and a bypass port 748. The pump 730 includes actuators corresponding to each of the above ports in order to flow fluid through only a single port at a time. In some embodiments, additionally or alternatively, the pump 730 may flow fluid through two or more ports simultaneously. As an example, blood may flow through the bypass port 748 while media flow through the media port 744. The flush port 742 and the media port 744 are fluidly coupled to the inlet 704. The flush port may provide saline while the media port 744 may provide media (e.g., including one or more cell nutrients). The blood port 746 is also fluidly coupled to the inlet 704. The bypass port 748 is fluidly coupled to a bypass passage, which directs patient blood away from the fluid manifold. In one example, the bypass passage may redirect blood back to a patient. In this way, manifold 740 may be referred to herein as a multi-fluid manifold that connects various fluid ports flowing various fluids (e.g., saline, media, and blood) to a fluid manifold and fluid channels of the stem cell organ device. Control of the pump 730 may adjust which type of fluid, through a corresponding port of the manifold 740, flows into and through the fluid channels of the stem cell organ device.

FIGS. 8-13A-C show an embodiment of a stem cell organ device which includes separated loading layers (including inlet manifolds) and channel layers (including stem cell or fluid channels). The separated layers may stack on top of one another. The stem cell organ device described in FIGS. 8-13A-C may function similarly to the other stem cell organ devices described herein with reference to FIGS. 1-7.

Figure 8:
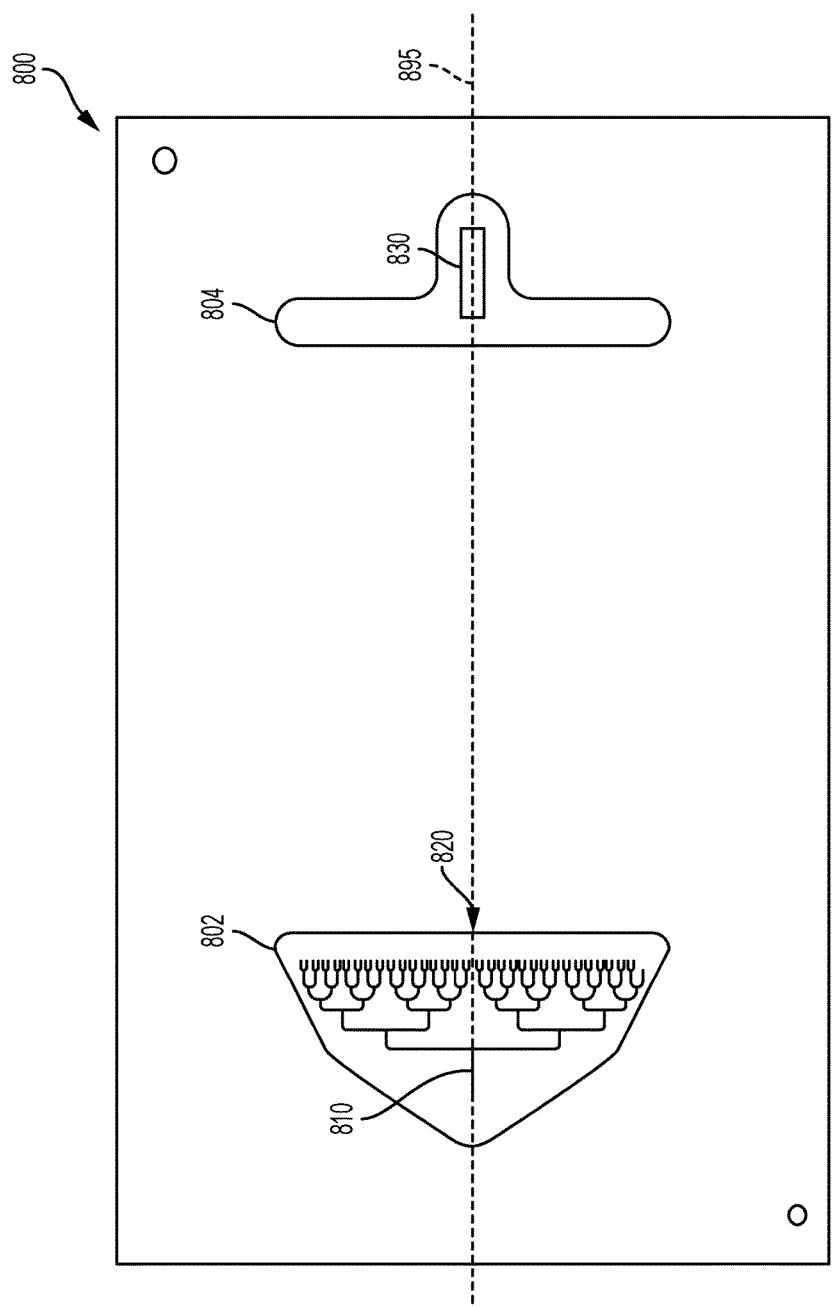
FIG. 8 shows a perspective view of a stem cell loading layer of an embodiment of a stem cell organ device.

FIG. 8 shows a stem cell loading layer 800. Stem cells may be loaded into the stem cell loading layer 800, as described above. The stem cell loading layer 800 comprises an inlet manifold 802 opposite an outlet manifold 804. The inlet manifold 802 comprises an inlet 810, which is a single pathway leading to loading channels 820. The loading channels 820 bifurcate into a plurality of channels. In one example, a volume of the loading channels 820 may decrease by a factor of two following each bifurcation. Decreasing the volume in this way allows a channel upstream of a bifurcation to be substantially equal in volume to the two channels downstream of the bifurcation. In another example, the width of the loading channels 820 may remain substantially constant following bifurcation.

The outlet manifold 804 comprises an outlet 830 for discharging stem cells, or excess media loaded with the stem cells, from the stem cell loading layer 800. The outlet 830 aligns with a central axis 895 of the stem cell loading layer 800. The stem cell loading layer 800 is symmetric about the central axis 895. In the current embodiment, the outlet 830 is rectangular. In other embodiments, the outlet 830 may be square, circular, triangular, diamond, elliptical, etc. In alternate embodiments, the inlet 810 and outlet 830 may not be aligned with the central axis 895 and may instead be offset from and arranged on opposite sides of the central axis 895.

The outlet manifold 804 is located on an opposite side of the stem cell loading layer 800 compared to the inlet manifold 802. The manifolds are completely separated by a length of the stem cell channels 820. In this way, stem cells may not flow directly from the inlet manifold 802 to the outlet manifold 804.

Figure 9:
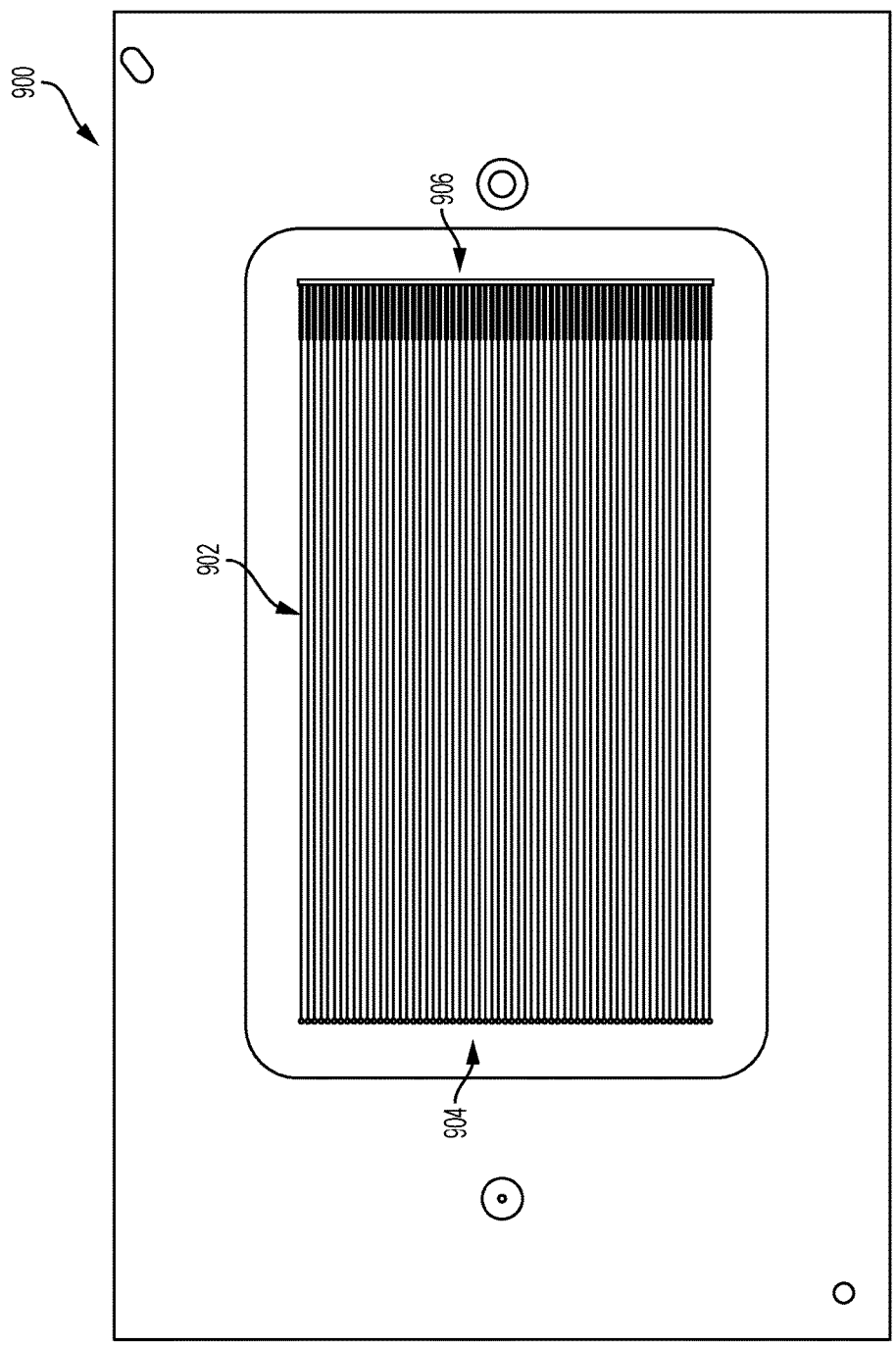
FIG. 9 shows a perspective view of a stem cell channel layer of an embodiment of a stem cell organ device.

FIG. 9 shows a stem cell channel layer 900 comprising a plurality of stem cell channels 902, inlets 904, and sieves 906. The stem cell channel layer 900 is located directly below and in face-sharing contact with the stem cell loading layer 800 of FIG. 8. The stem cell channels 902 align with the stem cell loading channels 820 of FIG. 8. Specifically, ends of the stem cell loading channels 820 align with the inlets 904. The inlets 904 guide stem cells one at a time through the stem cell channels 902. Sieves 906 are located at an end of the stem cell channels 902 opposite the inlets 904. The sieves may prevent stem cells from flowing out of the stem cell channels 902, while allowing ions, fluids, etc. to flow through its openings. Media flowing through the sieves 906 may flow into the outlet manifold 804 of FIG. 8. The stem cell channels 902 are linear as shown, but may be other suitable shapes in other embodiments.

Figure 10:
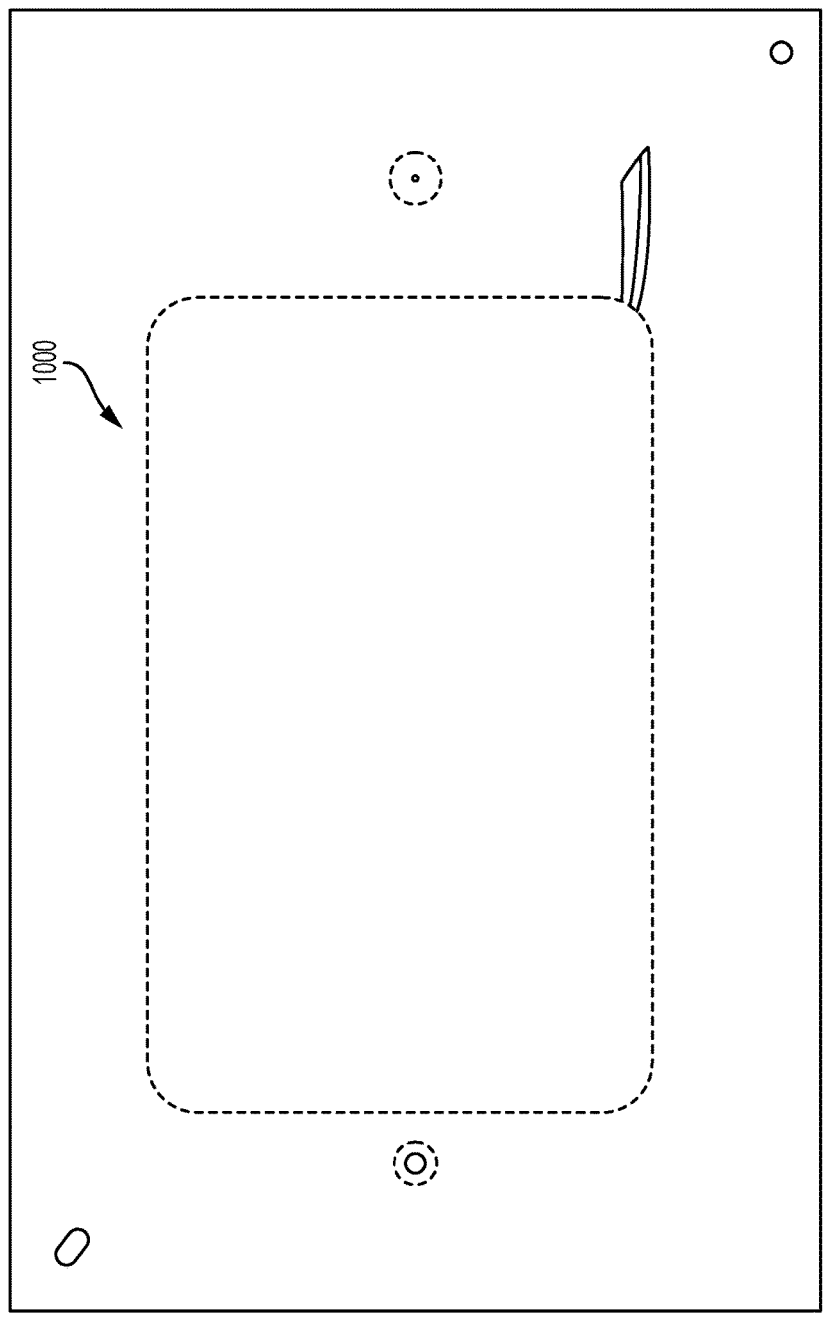
FIG. 10 shows a perspective view of a membrane layer of an embodiment of a stem cell organ device.

FIG. 10 shows a membrane 1000 composed of a selective barrier (semi-permeable membrane) capable of allowing the transfer of select small molecules, ions, etc. The membrane 1000 is directly below the stem cell channel layer 900. In one example, the membrane 1000 may allow water, salts (Na, K, Ca, etc.), sodium bicarbonate, urea, and other small molecules to pass between stem cell channels and fluid channels. Furthermore, the membrane 1000 may prevent passage of red blood cells, large proteins, and other large molecules. In this way, the membrane 1000 may comprise pores (not shown) with a diameter corresponding smaller molecules. In another example, the membrane 1000 may comprise charged pores and allow passage of similarly charged molecules. Additionally or alternatively, the membrane 1000 may allow passage of molecules based on polarity, wherein a molecule with a higher polarity may pass through the membrane 1000 faster than a molecule with a lower polarity. The aforementioned molecules flow down a concentration gradient through the membrane 1000. In one example, water and salt may flow from blood, through the membrane 1000, and into the stem cell channels 902 of FIG. 9 as long as a concentration of the above compounds in the stem cell channels is lower than a concentration in the fluid channels.

Figure 11:
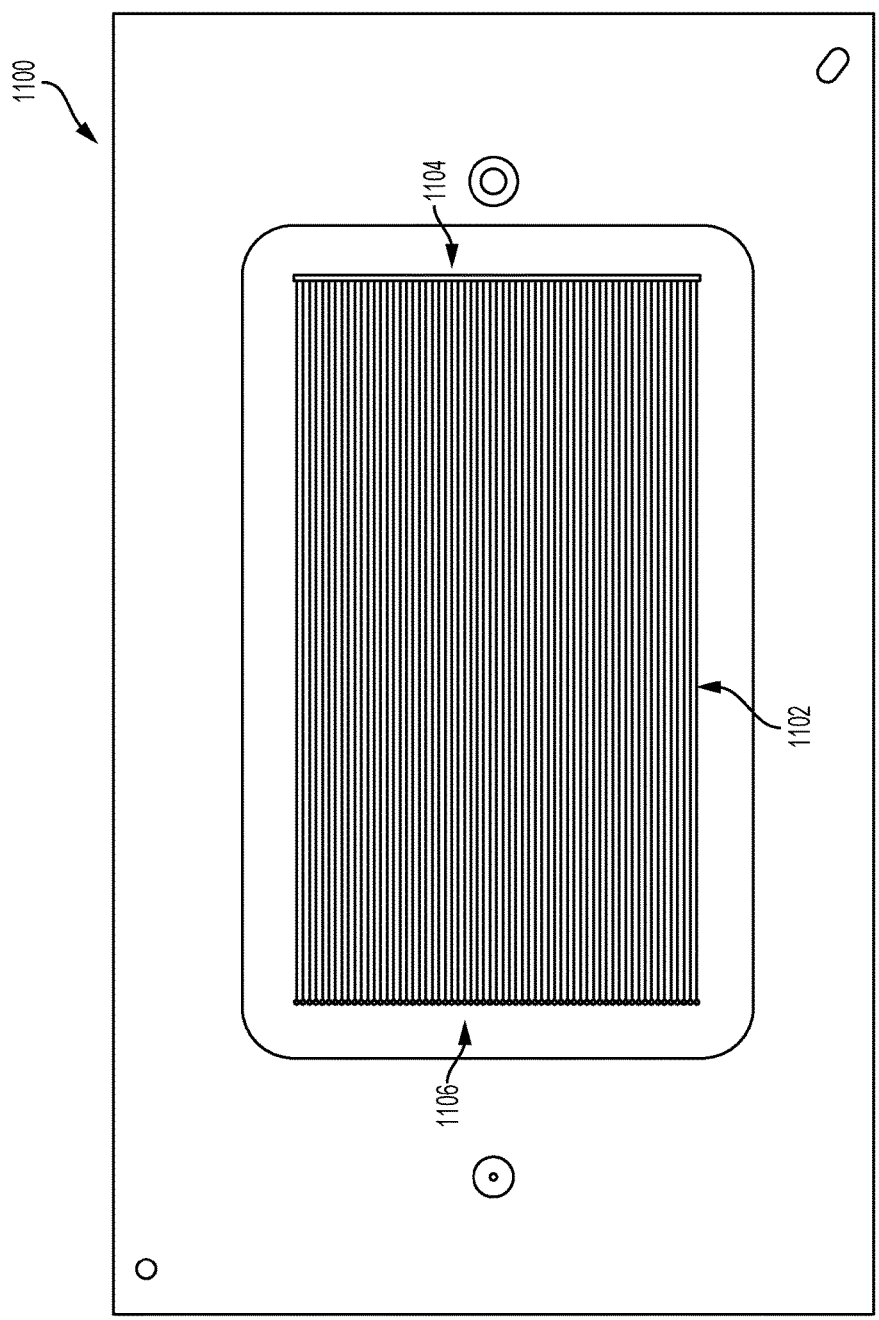
FIG. 11 shows a perspective view of a fluid channel layer of an embodiment of a stem cell organ device.

FIG. 11 shows a fluid channel layer 1100 comprising a plurality of fluid channels 1102. The fluid channels 1102 may minimize an area of turbulence and stagnation, as well as blood-air interfaces in order to decrease a likelihood of blood clotting. An inlet 1104 and an outlet 1106 are located on opposite sides of the fluid channels 1102. In one example, the inlet 1104 may be on an opposite side of a stem cell organ device compared to the inlets 904 of FIG. 9 of the stem cell channels 902. In this way, a pump may load stem cells and blood 180° out of phase with respect to a direction of flow. In an alternate embodiment, the inlet 1104 may be on a same side of the stem cell organ device as the inlets 904 of FIG. 9 of the stem cell channels 902.

The fluid channels 1102 do not comprise sieves. Blood may flow out the outlet 1106 back to a patient. As discussed above, when not treating the patient's blood, an alternate fluid such as saline or media, may flow through the fluid channels 1102. The fluid channel layer 1100 is located directly below the membrane 1000. In this way, the fluid channel layer 1100 may communicate with the stem cell channel layer 900 through the membrane 1000. In this way, the fluid channel layer 1100 and the stem cell layer 900 are physically separated while being fluidly coupled through the membrane 1100. The fluid channels 1102 may align with the stem cell channels 902. This allows blood to flow directly below and in-line with the stem cells loaded into the stem cell channels 902. In one example, a number of fluid channels 1102 may be exactly equal to a number of stem cell channels 902. The fluid channels 1102 are linear as shown, but may be other suitable shapes in other embodiments.

Figure 12:
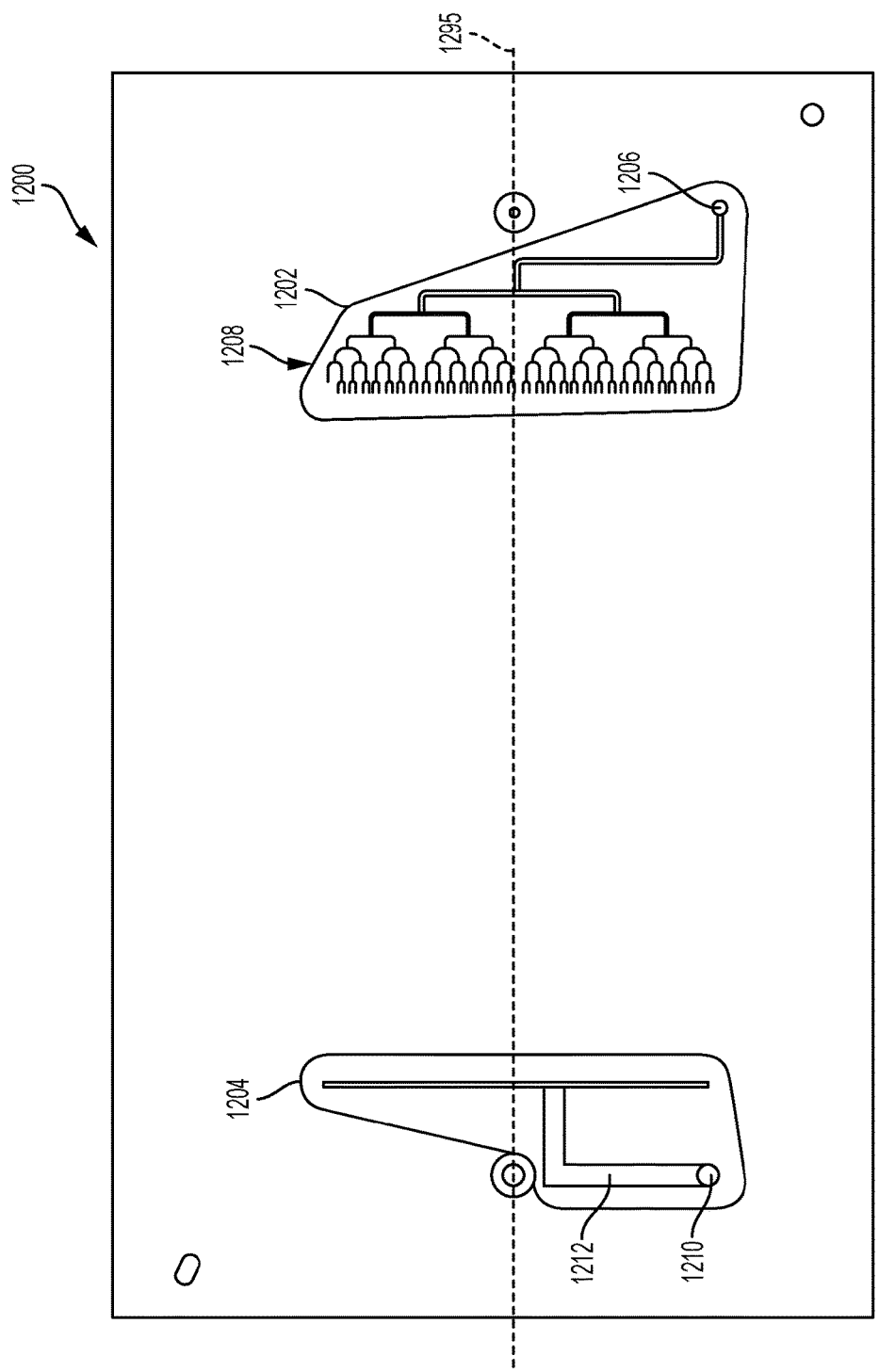
FIG. 12 shoes a perspective view of a fluid loading layer of an embodiment of a stem cell organ device.

FIG. 12 shows a fluid loading (e.g., feed) layer 1200 with an inlet manifold 1202 and an outlet manifold 1204. The inlet manifold 1202 comprises an inlet 1206 fluidly coupled to fluid loading channels 1208. The fluid loading channels 1208 originate as a single channel fluidly coupled to the inlet 1206 before bifurcating to a plurality of fluid loading channels 1208 equal to the number of fluid channels 1102 of FIG. 11. The inlet 1206 does not align with a central axis 1295 of the fluid loading layer 1200. An outlet 1210 is aligned with the inlet 1206 and thus, also misaligned with the central axis 1295. In alternate embodiments, the inlet 1206 and outlet 1210 may be offset from the central axis 1295 by varying amounts and the inlet 1206 and outlet 1210 may be positioned on opposite sides of the central axis 1295.

An outlet passage 1212 leads to the outlet 1210. The fluid loading layer 1200 is located directly below the fluid channel layer 1100 of FIG. 11. In this way, fluid from the fluid loading channels 1208 flow ups into the fluid channels 1102, where the fluid flows along an entire length of the fluid channels 1102 before flowing down into the outlet passage 1212 and out the outlet 1210.

The fluid inlet manifold 1202 is physically and fluidly separated from the fluid outlet manifold 1204. The manifolds are located on opposite sides of the fluid loading layer 1200. The fluid inlet manifold 1202 is located below the stem cell outlet manifold (e.g., stem cell outlet manifold 804 of FIG. 8) along a common vertical axis. The fluid outlet manifold 1202 is located below the stem cell inlet manifold (e.g., stem cell inlet manifold 802 of FIG. 8).

FIGS. 7-12 depict various embodiments of the above described stem cell organ device. In one example, the stem cell organ device may comprise two laser cut polymer layers to transport stem cells to the stem cell channels. A top glass plate may be used for support and visualization of the stem cell channels. Additionally or alternatively, a bottom glass plate may also be used such that light may shine through an entirety of the stem cell organ device. The stem cell organ device may further comprise an inlet header, where the inlet header is a binary fractal structure to aid in guiding the stem cells to evenly load the stem cell channels. The stem cell channel exits may comprise a sieve to trap the stem cells while allowing media, saline, or other bulk fluids to pass through the stem cell channel. Stem cells and/or bulk fluid may be introduced to the stem cell channels via the inlet header. The inlet header may operate in a manner similar to the inlet manifold described above.

FIG. 13A shows a cross-section 1300A of loading channels 1302A interfaced with channels 1304A. The channels may be stem cell channels or fluid channels (which may flow media, blood, or saline). As shown, the loading channels 1302A are oblique to the channels 1304A prior to insertion points 1306A. The channels overlap at the insertion point, as will be described in greater detail with respect to FIG. 13CA.

FIG. 13B shows a cross-section 1300B of channel 1304B interfaced with outlets 1308B. As shown, the channel 1304B is a single, larger passage compared to the channels 1304A of FIG. 13A. In one example, the channels 1304A may merge to form the channel 1304B. The channel interfaces with the outlets 1308B, which lead to an outlet chamber 1310B.

FIG. 13C shows a cross-section 1300C of a stem cell loading channel 1302C fluidly coupled to a stem cell channel 1304C. An axes system 1395C comprises two axes, a vertical axis and a horizontal axis. The loading channel 1302 may be used similarly to one of the loading channels 820 of FIG. 8. The stem cell channel 1304 may be used similarly to one of the stem cell channels 902. The loading channel 1302C and the channel 1304C are both parallel to the horizontal axis. Stem cells flow from the loading channel 1302C along the horizontal axis, down into the stem cell channel 1304C along the vertical axis at an insertion point 1306C, and back along the horizontal axis through the stem cell channel 1304C. In this way, a direction of stem cell flow turns 90° twice in order to load the stem cell channels. A flow direction of stem cells in the channels is parallel. By turning prior to entering the channel 1304C, air bubbles may be removed due to the sudden directional change in stem cell flow, which may provide more even stem cell loading into the channel 1304C.

FIG. 14 depicts a method for loading stem cells into the stem cell channels and operating a stem cell organ device, such as any of the stem cell organ devices described herein with reference to FIGS. 1-13A-C and 16-20.

Turning now to FIG. 14, a method 1400 for loading stem cells into a plurality of stem cell channels of a stem cell organ device and operating the stem cell organ device is illustrated. The method 1400 further describes determining stem cell degradation within the device.

The method 1400 begins at 1402 which includes injecting stem cells and media into the stem cell channels. Each stem channel may include a sieve, as described above, in order to contain the stem cells in the stem cell channel while allowing the media, containing nutrients and used to grow the stem cells, to flow through the sieve and out of the stem cell channel. The method at 1402 may further include, at the same time as injecting the stem cells and media into the stem cell channels, flowing (e.g., at a flow rate below a threshold) additional media containing various cell nutrients through the fluid channels of the stem cell organ device. In some examples, before loading the stem cells into the stem cell channels at 1402, both the stem cell channels and fluid channels may be primed with a fluid (such as saline and/or various cell nutrients) for a duration (e.g., 1-2 days). For example, the stem cell organ device may be primed (and loaded) with the fluid simultaneously from both sides (from both the stem cell channel side and the fluid channel side) in order to reduce the likelihood of rupture of the membrane separating the stem cell channels and fluid channels.

At 1404, the method 1400 includes determining if a stem cell channel is fully loaded. The stem cell channel may be fully loaded when the stem cells fill an entirety of the stem cell channel. This may be indicated via the clear and/or transparent window pane coupled to or above the stem cell channels, as described above and below, such that a patient may visually determine if the stem cell channels are fully loaded. Alternatively, the stem cell organ device may comprise an indicator capable of indicating an amount of stem cells in the stem cell channel.

If the stem cell channels are not full, then the method 1400 proceeds to 1406 to continue loading stem cells into the stem cell channels until the stem cell channels are fully loaded. If the stem cell channels are fully loaded, then the method 1400 continues to 1408 to disable the stem cell flow to the stem cell channels. This may include capping an inlet or inlet to port to all of the stem cell channels and/or disabling a stem cell pump (or injector) coupled to the inlet port of the stem cell channels.

At 1409, the method 1400 includes continuing to flow cell media to and through the fluid channels prior to a patient blood flow through the fluid channels. In this way, the stem cells may continue to receive nutrients from the media (through the membrane) in order to increase stem cell viability and keep the stem cells alive.

At 1410, the method 1400 includes flushing the fluid channels with saline (or an alternate flushing solution) in order to remove the media used to grow the stem cells from the fluid channels.

At 1412, the method 1400 includes, after connecting the stem cell organ device to a patient, continuously flowing the blood of the patient into the fluid channels of the stem cell organ device. During operation of the stem cell organ device, the blood is continuously cycled through the fluid channels while the stem cells remain in the stem cell channels. By flowing blood into the fluid channels, the blood and the stem cells begin to transfer ions, salts, and toxins down their respective concentration gradients (e.g., flow from high concentration to low concentration). For example, toxins flow from the blood to the stem cells while nutrients such as sodium and potassium may flow from the stem cells to the blood.

At 1414, the method 1400 includes monitoring and/or assaying the stem cells in order to determine a viability of the stem cells within the stem cell channels. As described above, the stem cells may be monitored via visualization or they may be assayed via a HPLC or other suitable cell assay devices. In one example, the viability of the stem cells may be continuously monitored throughout the duration of device use.

At 1416, the method 1400 includes determining if the stem cells are viable (or if stem cell viability is over a threshold). If the stem cells are not viable (e.g., viability of the stem cells decreases below the threshold which may be based on a cell viability model), the method proceeds to 1418 to discontinue blood flow through the fluid channels. The stem cell organ device may then be disconnected from the patient and flow circuit and replaced with a new, unloaded (e.g., empty device without stem cells) or viable stem cell organ device (containing already grown and viable stem cells).

Alternatively, if the stem cells are viable, the method continues to 1420. At 1420, the method 1400 includes determining if blood flow treatment (e.g., therapy) is complete. Blood flow treatment may be complete via measuring a biomarker indicating a blood purity greater than a threshold purity. For example, a blood sample may indicate a blood toxin concentration being less than a threshold toxin concentration, thereby increasing the blood purity to a blood purity greater than the threshold purity.

If the blood flow treatment is not complete, then the method 1400 proceeds to 1422 to continue flowing blood through the fluid channels of the stem cell organ device. The blood flow may continue to be monitored until treatment of the blood flow is complete. If the blood flow treatment is complete, then the method 1400 proceeds to 1424 to stop flowing blood, flush the fluid channels with saline, and then to begin flowing media through the fluid channels. By flowing saline into the fluid channels, the blood is removed from the fluid channels. By flowing media to the fluid channels, the stem cell viability may be maintained until a subsequent treatment session is requested. In this way, the stem cells may be maintained within a viable state and used in future patient treatments.

FIG. 15A including a method 1500 for a portable stem cell organ device is shown. This allows the patient to conduct routine daily activities (e.g., walk, drive, work, etc.) without worrying about dialysis at a doctor's office. The stem cell device comprises a programmable pump capable of pumping a variety of fluids into and out of the stem cell device to maintain a desired operation of the stem cell device with little to no input from the patient. The method 1500 may be conducted before, during, or after method 1400 of FIG. 14.

Method 1500 begins at 1502, initiating operation of a multi-fluid manifold (e.g., fluid manifold 740 of FIG. 7) of the stem cell device. The multi-fluid manifold may be coupled to or part of a fluid inlet manifold (e.g., fluid inlet manifold 1202 of FIG. 12 or fluid inlet manifold 1702 of FIG. 17) of the stem cell organ device. In one example, initiating operation may include turning on a variable pump (e.g., pump 730 of FIG. 7) fluidly coupled to the multi-fluid manifold. As explained above, the multi-fluid manifold may be fluidly coupled to a plurality of fluid channels of the stem cell organ device. The multi-fluid manifold may comprise a plurality of ports, wherein each of the ports may correspond to a different function. In one example, the multi-fluid manifold may comprise four different ports corresponding to four different stem cell device modes. A first port may correspond to a bypass mode, a second port may correspond to a blood mode, a third port may correspond to a media mode, and a fourth port may correspond to a flush mode. In some examples, additionally or alternatively, the multi-fluid manifold may comprise a fifth port corresponding to a cleaning mode. In other examples, cleaning may be conducted via the fourth port and thus may utilize the same fluid used in the flush mode. The pump may be electronically controlled by a controller electrically actuating actuators of the pump based on a desired mode of operation. Thus, the pump may comprise actuators corresponding to each of the ports of the multi-fluid manifold.

At 1504, the method 1500 determines if stem cells are loaded into the stem cell organ device. If the stem cells are not loaded, then the method 1500 proceeds to 1506 and enters the media mode and bypass mode. For example, the method at 1504 may include switching operation of the pump and multi-fluid manifold to the media mode and bypass mode, which are explained in more detail below with reference to the method at 1508.

At 1508, the method 1500 includes flowing media through the fluid channels while bypassing blood around (and not through) the fluid channels of the stem cell organ device. This may include the pump directing media through the third port to the fluid channels (e.g., fluid channels 802 of FIG. 8 or fluid channels 1704 of FIG. 17). The pump also directs blood through a bypass passage by flowing blood through the first port and flowing blood back to a patient without flowing blood to the stem cell organ device and through the fluid channels. This prevents blood from being filtered and may be used during conditions when blood mode conditions are not met. During the method at 1504, stem cells may be loaded into the stem cell channels of the stem cell organ device following method 1400 presented at FIG. 14 (e.g., according to the methods at 1402-1408).

In some embodiments, additionally or alternatively, the method 1500 may assay the stem cells prior to loading the stem cells in order to determine if the stem cells are viable. The assaying may be conducted by an optical sensor which may determine a color, absorbance, density (number of stem cells) of the stem cells as will be described below.

Returning to 1504, if the method 1500 determines that the stem cells are loaded, then the method 1500 proceeds to 1510 to determine if the fluid channels have been flushed with a desired fluid (such as saline or some other flushing solution) following flowing media through the fluid channels. If the fluid channels have not been flushed yet to remove the media, then the method 1500 proceeds to 1512 to enter the flush mode and the bypass mode, as described further below with reference to 1514.

At 1514, the method 1500 includes initiating the flush mode by flowing a flush solution (e.g., saline) to and through the fluid channels of the device. This may include the pump directing the flush solution through the fourth port of the multi-fluid manifold to the fluid channels. As an example, the pump may direct a volume of flush solution equal to the volume of the fluid channels. As another example, the pump may direct a volume of flush solution greater than the volume of the fluid channels. The method at 1514 also includes directing (via the pump) blood through the bypass passage by flowing blood through the first port and flowing blood back to the patient without flowing blood to the stem cell organ device and through the fluid channels.

Returning to 1510, if the method 1500 determines the fluid channels have been flushed with the flush solution, then the method 1500 proceeds to 1516 to enter the blood mode. The blood mode includes the pump directing blood through the second port, where the blood flows to the fluid channels. Blood is returned to the patient after flowing through the stem cell organ device. In this way, two blood passages to the patient exist, the bypass passage and a blood mode passage. The blood mode includes flowing the blood at a desired rate. Blood flow below the desired rate may increase a likelihood of blood coagulating and blood flow above the desired rate may decrease diffusion of molecules from the blood to the stem cells.

At 1518, the method 1518 includes filtering blood with the stem cells via the membrane separating the fluid channels flowing the blood and stem cell channels containing the stem cells. This may include the pump continuously flowing blood through the fluid channels of the stem cell device via the second port of the multi-fluid manifold. As described above, during blood filtering, the stem cells are stagnant in the stem cell channels. Thus, the pump does not direct stem cells through the third port during blood mode operation. Molecules pass through the membrane between the stem cells and the blood. As described above, salt, water, toxins, and other molecules may pass from the blood to the stem cells, while nutrients and other molecules may pass from the stem cells to the blood.

At 1520, the method 1500 includes determining if the stem cells are viable. The stem cells may be viable based on characterizations determined by the optical sensor described above. In one example, additionally or alternatively, the patient may visibly determine if the stem cells are viable by looking through a glass cover of the stem cell organ device and determining if a color change has occurred. In another example, the stem cell organ device may indicate stem cell degradation based on the optical sensor reading. The indication may include a visual and/or audible indication. For example, a light may be activated and/or a beeping sound may occur. Additionally or alternatively, the stem cell organ device may vibrate in response to the stem cells no longer being viable (e.g., degraded).

If the stem cells are degraded, then the method 1500 proceeds to 1522 to disable the blood mode and return the blood to the patient. The method at 1522 may also include stopping patient treatment and disconnecting the stem cell organ device so that it may be replaced with another device containing viable cells.

Returning to 1520, if the method 1500 determines stem cells are still viable, then the method 1500 proceeds to 1526 to determine if blood if fully filtered. An optical sensor, which may be the same optical sensor used to characterize the stem cells, may measure salt concentration, water concentration, toxin concentration, and other suitable properties for determining if the blood is fully filtered. In one example, the salt, water, and toxin concentrations may all be less than a corresponding threshold concentration. If the blood is not fully filtered, then the method 1500 proceeds to 1527 to continue operating in the blood mode until the blood is fully filtered.

If the blood is fully filtered, then the method 1500 proceeds to 1528 to exit the blood mode and returns blood back to the patient. Exiting the blood mode includes no longer flowing blood to the stem cell organ device. The method 1500 may no longer flow blood to the multi-fluid manifold.

At 1530, the method 1500 includes determining if the stem cells are still viable, as described above. In one example, the stem cell device may continuously measure stem cell viability. If the stem cells are no longer viable, the method 1500 proceeds to 1532 to disconnect the stem cell organ device from the treatment system so that it may be replaced with another device containing viable cells.

If the stem cells are still viable, then the method 1500 proceeds to 1534 to enter the media mode, as described above with reference to the methods at 1506 and 1508. For example, the pump may flow media through the fluid channels to provide nutrients to the stem cells and keep them alive until a following treatment event.

FIGS. 16-17 show a stem cell layer 1600 and fluid layer 1700 of another embodiment of a stem cell organ device which may operate similarly to the other stem cell organ devices described above. The stem cell layer 1600 shown in FIG. 16 and the fluid layer 1700 shown in FIG. 17 are separated from one another via a membrane (e.g., such as membrane 1000 shown in FIG. 10).

At least one stem cell layer 1600, at least one membrane, and at least one fluid layer 1700 may be combined together to form a stem cell organ device unit, such as the stem cell organ device unit shown in FIGS. 18-20. In one embodiment, the stem cell organ device unit may include multiple stem cell layers, membranes, and fluid layers arranged in an alternating fashion, as described above. In another embodiment, the stem cell organ device unit may only include a single stem cell layer, a single membrane, and a single fluid layer.

FIG. 16 shows the stem cell layer 1600 including a stem cell inlet manifold 1602, a plurality of stem cell channels 1604, and a stem cell outlet manifold 1606 all arranged in the same plane (e.g., plane of the layer). The stem cell inlet manifold 1602 includes an inlet 1608 and a plurality of branched loading channels 1610. The loading channels 1610 branch from the inlet 1608 to inlets of each individual stem cell channel 1604. The stem cell outlet manifold 1606 includes an outlet (or outlet passage) 1614 coupled to a plurality of sieves 1616 which are coupled to the plurality of stem cell channels 1604.

As shown in FIG. 16, the inlet 1608 and outlet 1614 are each offset from a central axis 1612 of the stem cell layer (which may be a common central axis for the stem cell layer, fluid layer, membrane, and entire stem cell organ device unit). Specifically, the inlet 1608 is arranged on an opposite side of the stem cell layer 1600 from the outlet 1614, relative to (and across from) the central axis 1612. This offset nature of the inlets and outlets of the stem cell layer 1600 and fluid layer 1700 (as discussed further below) may reduce pressure within the device and reduce sagging of the membrane and restriction of flow within the device (e.g., in the fluid channels). In alternate embodiments, the inlets and outlets of the stem cell layer and fluid layer may be offset from the central axis 1612 by a larger or smaller amount (e.g., distance from the central axis) than shown in FIGS. 16 and 17.

FIG. 17 shows the fluid layer 1700 including a fluid inlet manifold 1702, a plurality of fluid channels 1704, and a fluid outlet manifold 1706 all arranged in the same plane. The fluid inlet manifold 1702 includes an inlet 1708 and a plurality of branched loading channels 1710. The loading channels 1710 branch from the inlet 1708 to inlets of each individual fluid channel 1704. The inlet 1708 may be coupled to a multi-fluid manifold (e.g., such as multi-fluid manifold 740 shown in FIG. 7). The fluid outlet manifold 1706 includes an outlet (or outlet passage) 1714 coupled to a plurality of outlets 1716 of the plurality of fluid channels 1704.

As shown in FIG. 17 and introduced above, the inlet 1708 and outlet 1714 are each offset from the central axis 1612 of the fluid layer (which may be a common central axis for the stem cell layer, fluid layer, membrane, and entire stem cell organ device unit). Specifically, the inlet 1708 is arranged on an opposite side of the fluid layer 1700 from the outlet 1714, relative to (and across from) the central axis 1612. As shown in FIGS. 16 and 17, the inlet 1608 and inlet 1708 are aligned with one another on a same, first side of the device relative to the central axis 1612 and the outlet 1614 and outlet 1714 are aligned with one another on a same, second side of the device relative to the central axis 1612. Thus, a direction of flow of stem cells through the stem cell channels 1604 when loading the device with stem cells may the same as a direction of flow of fluid through the fluid channels 1704.

FIGS. 18-20 show an embodiment of an assembled stem cell organ device unit 1802 containing at least one stem cell layer (such as the stem cell layer 1600 shown in FIG. 16), at least one membrane (such as the membrane 1000 shown in FIG. 10), and at least one fluid layer (such as fluid layer 1700 shown in FIG. 17). Specifically, FIG. 18 shows a top perspective view 1800 of the stem cell organ device unit 1802 with the fluid layer visible at the top of the unit. FIG. 19 shows a side perspective view 1900 of the stem cell organ device unit 1802 with the stem cell layer visible. FIG. 20 shows a side view 2000 of the stem cell organ device unit 1802.

The stem cell organ device unit 1802 shown in FIGS. 18-20 includes a top plate 1803, a bottom plate 1804, and a plurality of layers 1806. The plurality of layers 1806 may include at least one of each of the stem cell layer, the fluid layer, and the membrane. Specifically, the membrane is positioned between the stem cell layer and fluid layer and all three layers 1806 are sandwiched between the top plate 1803 and the bottom plate 1804. The top plate 1803 and bottom plate 1804 are physically and fluidly secured to one another such that no fluid exits the sides of the device via a plurality of fasteners (e.g., screws and nuts) 1808 positioned through aligned apertures of the top and bottom plates and the layers 1806. The plurality of fasteners 1808 are positioned around an outer perimeter of the stem cell organ device unit 1802. The top plate 1803 and bottom plate 1804 may be made of a transparent material (e.g., glass or plastic) such that a user may visualize the layers within the unit. As such, a user may visualize fluid flow and/or stem cell viability of the unit.

The stem cell organ device further includes a fluid inlet port 1810 which is fluidly coupled to the fluid inlet (e.g., inlet 1708 of FIG. 17) of the fluid layer and is configured to couple to a fluid pump and/or multi-port manifold of the stem cell organ device. The stem cell organ device also includes a fluid outlet port 1812 which is fluidly coupled to the fluid outlet (e.g., outlet 1714 of FIG. 17) of the fluid layer. The stem cell organ device further includes a stem cell inlet port 1902 (shown in FIG. 19) fluidly coupled to the stem cell inlet (e.g., inlet 1608 of FIG. 16) of the stem cell layer and a stem cell outlet port 1904 (also shown in FIG. 19) fluidly coupled to the outlet (e.g., outlet 1614 of FIG. 16) of the stem cell layer.

A complete stem cell organ device may include one or more stem cell organ device units, such as the stem cell organ device unit shown in FIGS. 18-20. In one embodiment, the stem cell organ device may include a plurality (e.g., at least two) of stem cell organ device units coupled in series with one another such that fluid (such as blood) flows through a first stem cell organ device (from the inlet to outlet) and then through at least a second stem cell organ device (from the inlet to outlet). In another embodiment, the stem cell organ device may include a plurality (e.g., at least two) of stem cell organ device units coupled in parallel with one another such that fluid (such as blood) flow simultaneously, in parallel, through multiple stem cell organ device units. The arrangement (e.g., series or parallel) and number of stem cell organ device units of the complete stem cell organ device may be selected based on a desired clearance level (e.g., desired amount of transfer of toxins and nutrients between the cells and blood within the device), duration of device use (e.g., treatment period or duration where a patient's blood is being filtered by the stem cells loaded within the device), and/or cell type.

In an experimental efficacy study, a plurality of stem cell organ device units (such as the units shown in FIGS. 18-20) were loaded with a plurality of stem cells. The stem cells used in the study were from a human hepatoma cell line (HepG2). However, alternate cell types may have been used as well. After a period of first priming the device with saline and/or media, the unit was loaded with the stem cells. The stem cells were allowed to grow and attach to the membrane as media was flowed through the fluid channels of the fluid layer of the unit for a period of 14-25 days. Each day, an assay assessing the function and viability of the cells within the unit was taken. Common proteins secreted by living HepG2 cells include the plasma protein albumin and Apo lipoprotein (ApoB). FIGS. 21-23 show graphs of protein levels (measured in weight/volume) measured over a period of days following loading the unit with the stem cells. Specifically, FIG. 21 shows a first graph 2100 of ApoB protein secreted by stem cells of a first stem cell organ test device over a period of 14 days, FIG. 22 shows a second graph 2200 of albumin secreted by the stem cells of the first stem cell organ test device over a period of 14 days, and FIG. 23 shows a third graph 2300 of ApoB protein secreted by stem cells of a second stem cell organ test device over a period of 25 days. The graphs in FIGS. 21-23 show that the functionality of the HepG2 stem cells were maintained within the stem cell device unit through the duration of the study as evidenced by the steady increase of secretion from Day 1 to the end point (Day 14 or day 25) of both ApoB and albumin.

In this way, stem cells may be grown to mimic a variety of organs (e.g., liver, pancreas, kidney, lung, etc.) and used to transfer ions and salts from the stem cells to blood of a patient via a stem cell organ device. The stem cell organ device may include a plurality of stem cell channels and a plurality of fluid channels, where the plurality of stem cell channels are separated from the plurality of fluid channels via a membrane. The stem cells are loaded into the stem cell channels of the stem cell organ device and kept alive via nutrient rich media. While the stem cells are loaded into the stem cell channels and before flowing blood through the device for patient treatment, media containing nutrients flow through the fluid channels of the stem cell organ device. The media is then flushed from the stem cell organ device with a flushing solution, such as saline, such that upon flowing blood into the stem cell organ device the fluid channels do not contain any leftover media. The blood and the stem cells may then exchange a variety of nutrients and molecules across the membrane separating the stem cell channels from the fluid channels. The membrane inhibits the exchange of stem cells into the fluid channels and blood into the stem cell channels. Blood is continuously flowed through the fluid channels while the stem cells are only flowed into the stem cell channels once before patient treatment The technical effect of loading a stem cell organ device with stem cells is to allow a patient in need of an organ transplant to receive medical treatment via stem cells mimicking the sought after organ. The stem cells are loaded into the stem cell device and used to exchange nutrients from the stem cells to the patient's blood while also transferring toxins and other unwanted components from the patient's blood to the stem cells.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A stem cell organ device, comprising:
   a first channel adapted to house a plurality of cells, wherein a width of the first channel is less than 100 µm;
   a second channel;
   a membrane arranged between the first channel and the second channel; and
   a first inlet manifold coupled to the first channel;
   wherein the first channel and the second channel comprise a plurality of ridges facing the membrane, wherein the ridges are of variable size and shape.

2. The device of claim 1, wherein one or more interior surfaces of the first inlet manifold include guides.

3. The device of claim 2, wherein the guides include a surface treatment applied to the one or more interior surfaces of the first inlet manifold.

4. The device of claim 2, wherein the guides include etchings positioned across portions of the one or more interior surfaces of the first inlet manifold.

5. The device of claim 4, wherein the etchings include one or more of sections of parallel lines, crisscrossing lines, overlapping lines, circles, swirls, and overlapping curved lines distributed over a surface of the one or more interior surfaces.

6. The device of claim 2, wherein the one or more interior surfaces includes a top surface and the top surface further includes an inlet port for flowing cells into the first inlet manifold.

7. The device of claim 1, further comprising an outlet manifold coupled to the first channel and a sieve including a plurality of apertures, where the sieve is positioned across an opening between the first channel and the outlet manifold.

8. The device of claim 1, further comprising a second inlet manifold coupled to the second channel, where the second inlet manifold is fluidly coupled to a multi-port manifold including at least three ports configured to flow different fluids from a pump, the pump fluidly coupled to the multi-port manifold, and through the second channel.

9. A stem cell organ device, comprising:
   a first layer including a first plurality of channels adapted to house a plurality of cells;
   a second layer including a second plurality of channels, where each channel of the second plurality of channels is aligned with a corresponding channel of the first plurality of channels;
   wherein a width of each of the plurality of channels is less than 100 µm; and
   a semi-permeable membrane positioned between the first layer and the second layer;
   wherein each of the plurality of channels comprises a plurality of ridges facing the semi-permeable membrane, wherein the ridges are of variable size and shape.

10. The stem cell organ device of claim 9, further comprising a multi-port manifold fluidly coupled to the second plurality of channels through an inlet and a plurality of branched loading channels of the second layer.

11. The stem cell organ device of claim 10, wherein the multi-port manifold comprises each of a flush port, a media port, a bypass port, and a blood port and further comprising a variable pump fluidly coupled to the multi-port manifold.

12. The stem cell organ device of claim 9, wherein the first layer includes:
   a first inlet manifold including a first plurality of branching loading channels branching from a single, first inlet of the first inlet manifold to the first plurality of channels; and
   a first outlet manifold including a first outlet fluidly coupled to each of the first plurality of channels.

13. The stem cell organ device of claim 12, wherein the second layer includes:
   a second inlet manifold including a second plurality of branching loading channels branching from a single, second inlet of the second inlet manifold to the second plurality of channels; and
   a second outlet manifold including a second outlet fluidly coupled to each of the second plurality of channels.

14. The stem cell organ device of claim 13, wherein the first inlet manifold and second inlet manifold are arranged on a same side of the stem cell organ device, wherein the first inlet and second inlet are offset from and positioned on opposite sides of a central axis of the stem cell organ device, where the central axis is arranged along a length of the first and second pluralities of channels, and wherein the first outlet and second outlet are offset from and positioned on opposite sides of the central axis.

15. The stem cell organ device of claim 13, wherein the second inlet manifold is fluidly coupled to fluid loading channels, wherein the fluid loading channels originate as a single channel fluidly coupled to the second inlet before bifurcating to a plurality of fluid loading channels.

16. The stem cell organ device of claim 12, wherein one or more interior surfaces of the first inlet manifold include guides.

17. The stem cell organ device of claim 16, wherein the guides include at least one of etchings, protrusions, grooves, ingots, or stamps positioned across portions of the one or more interior surfaces of the first inlet manifold.

18. The stem cell organ device of claim 16, wherein the guides are arranged in an unorganized manner across portions of the one or more interior surfaces of the first inlet manifold.

19. A stem cell organ device, comprising:
- a first layer including a first plurality of channels adapted to house a plurality of cells and a first inlet manifold, wherein a plurality of stem cell guides are interspersed on an inner surface of the first inlet manifold; and
- wherein the stem cell guides are at least one of an etching, protrusion, groove, ingot, or stamp;
- a second layer including a second plurality of channels, where each channel of the second plurality of channels is aligned with a corresponding channel of the first plurality of channels; and
- a semi-permeable membrane positioned between the first layer and the second layer.

* * * * *